(12) United States Patent
Miller et al.

(10) Patent No.: US 11,872,009 B1
(45) Date of Patent: Jan. 16, 2024

(54) BASELINING USER PROFILES FROM PORTABLE DEVICE INFORMATION

(71) Applicant: Tula Health, Inc., Kaysville, UT (US)

(72) Inventors: Devin Warner Miller, Morgan, UT (US); David Rich Miller, Morgan, UT (US)

(*) Notice: Subject to any disclaimer, the term of this patent is extended or adjusted under 35 U.S.C. 154(b) by 784 days.

(21) Appl. No.: 16/985,194

(22) Filed: Aug. 4, 2020

Related U.S. Application Data

(63) Continuation of application No. 16/445,017, filed on Jun. 18, 2019, now Pat. No. 10,765,320, which is a
(Continued)

(51) Int. Cl.
*G06F 1/16* (2006.01)
*A61B 5/00* (2006.01)
(Continued)

(52) U.S. Cl.
CPC .......... *A61B 5/0002* (2013.01); *A61B 5/0075* (2013.01); *A61B 5/02055* (2013.01);
(Continued)

(58) Field of Classification Search
CPC . A61B 5/0002; A61B 5/0075; A61B 5/02055; A61B 5/0537; A61B 5/14542;
(Continued)

(56) References Cited

U.S. PATENT DOCUMENTS 8,049,597 B1 11/2011 Murakami et al.
8,460,001 B1 6/2013 Chuang
(Continued)

FOREIGN PATENT DOCUMENTS

| WO | WO-2010109448 A1 * | 9/2010 | ........... A61B 5/0482 |
| WO | WO-2015065674 A1 * | 5/2015 | ............... A61B 5/01 |
| WO | WO-2019210117 A1 * | 10/2019 | ........... A61N 1/0534 |

OTHER PUBLICATIONS

Mariana Jacob Rodrigues, Physiological and Behavior Monitoring Systems for Smart Healthcare Environments, (2020,: Sensors 20.8: 2186. All pages. (Year: 2020).*

*Primary Examiner* — Michael T Tran
(74) *Attorney, Agent, or Firm* — Miller IP Law

(57) ABSTRACT

Methods, systems, apparatuses, and/or devices for determining a baseline for an individual. The methods, systems, apparatuses, and/or devices may include a first memory device for computer storage. The methods, systems, apparatuses, and/or devices may include a processing device coupled to the first memory device, where the processing device is configured to: receive profile information for a user; generate a user profile based on the profile information; query a set of baseline profiles stored at the first memory device or a second memory device to identify a subset of baseline profiles; aggregate baseline profile information from the first baseline profile and baseline profile information from the second baseline profile to obtain an aggregated baseline profile; and set a baseline for a physiological parameter of the user from which to measure against for the physiological parameter, wherein the baseline is based on the physiological parameter of the aggregated baseline profile.

18 Claims, 19 Drawing Sheets

Related U.S. Application Data continuation of application No. 14/981,246, filed on Dec. 28, 2015, now Pat. No. 10,368,744.

(60) Provisional application No. 62/192,998, filed on Jul. 15, 2015, provisional application No. 62/117,282, filed on Feb. 17, 2015.

(51) Int. Cl.

| | | |
|---|---|---|
| *A61B 5/0205* | (2006.01) | |
| *H04B 1/3827* | (2015.01) | |
| *A61B 5/145* | (2006.01) | |
| *A61B 5/0537* | (2021.01) | |
| *A61B 5/318* | (2021.01) | |
| *G06N 7/01* | (2023.01) | |

(52) U.S. Cl.
CPC ........ *A61B 5/0537* (2013.01); *A61B 5/14542* (2013.01); *A61B 5/318* (2021.01); *A61B 5/4875* (2013.01); *A61B 5/7275* (2013.01); *G06F 1/163* (2013.01); *G06N 7/01* (2023.01); *H04B 1/385* (2013.01); *A61B 2560/0242* (2013.01); *A61B 2562/0219* (2013.01)

(58) Field of Classification Search
CPC ..... A61B 5/318; A61B 5/4875; A61B 5/7275; A61B 2560/0242; A61B 2562/0219; G06F 1/163; G06N 7/01; H04B 1/385
USPC .............................................. 706/11; 700/92
See application file for complete search history.

(56) References Cited

U.S. PATENT DOCUMENTS

| | | | |
|---|---|---|---|
| 8,516,104 B1 | 8/2013 | Liu et al. | |
| 8,517,912 B2 | 8/2013 | Clare | |
| 8,784,115 B1 | 7/2014 | Chuang | |
| 9,132,839 B1 | 9/2015 | Tan | |
| 9,248,819 B1 | 2/2016 | Tan | |
| 9,495,126 B2 | 11/2016 | Lang | |
| 9,662,050 B2 | 5/2017 | Conrad et al. | |
| 9,788,797 B2 | 10/2017 | Rouquette | |
| 10,039,445 B1* | 8/2018 | Torch ................ A61B 5/18 |
| 10,368,744 B1* | 8/2019 | Miller ................ A61B 5/01 |
| 10,561,863 B1* | 2/2020 | Dashevsky .......... A61B 5/0836 |
| 10,650,916 B2* | 5/2020 | Moturu ................ G16H 20/40 |
| 2003/0229455 A1 | 12/2003 | Bevilacqua et al. | |
| 2004/0044547 A1 | 3/2004 | Klennert et al. | |
| 2005/0209512 A1 | 9/2005 | Heruth et al. | |
| 2006/0032315 A1 | 2/2006 | Saalastic et al. | |
| 2007/0179749 A1 | 8/2007 | Landrieve | |
| 2007/0253008 A1 | 11/2007 | Edge et al. | |
| 2007/0272011 A1 | 11/2007 | Chapa | |
| 2008/0146891 A1 | 6/2008 | Wang et al. | |
| 2009/0082692 A1* | 3/2009 | Hale ................ A61B 5/16 600/301 |
| 2009/0105560 A1 | 4/2009 | Soloman | |
| 2009/0203972 A1 | 8/2009 | Heneghan et al. | |
| 2011/0092779 A1 | 4/2011 | Chang et al. | |
| 2011/0169603 A1 | 7/2011 | Fithian et al. | |
| 2011/0245633 A1 | 10/2011 | Goldberg et al. | |
| 2012/0016435 A1* | 1/2012 | Rom ................ A61N 1/36082 607/45 |
| 2012/0066065 A1 | 3/2012 | Switzer | |
| 2012/0253484 A1* | 10/2012 | Burich ................ G16H 40/67 700/91 |
| 2012/0301887 A1 | 11/2012 | Bankaitis-Davis et al. | |
| 2012/0313776 A1 | 12/2012 | Utter, II | |
| 2013/0013327 A1 | 1/2013 | Horeseman | |
| 2013/0060720 A1 | 3/2013 | Burke | |
| 2013/0166580 A1 | 6/2013 | Marharajh et al. | |
| 2013/0297536 A1* | 11/2013 | Almosni ................ G16H 50/20 706/12 |
| 2014/0052567 A1 | 2/2014 | Bhardwaj | |
| 2014/0074824 A1 | 3/2014 | Rad et al. | |
| 2014/0107495 A1 | 4/2014 | Marinelli et al. | |
| 2014/0107498 A1 | 4/2014 | Bower et al. | |
| 2014/0125493 A1 | 5/2014 | Utter, II | |
| 2014/0127650 A1 | 5/2014 | Utter, II | |
| 2014/0207914 A1 | 7/2014 | Robinson | |
| 2014/0247155 A1 | 9/2014 | Proud | |
| 2014/0266787 A1 | 9/2014 | Tran | |
| 2014/0280890 A1 | 9/2014 | Yi et al. | |
| 2014/0309789 A1 | 10/2014 | Ricci | |
| 2014/0309868 A1 | 10/2014 | Ricci | |
| 2014/0313989 A1 | 10/2014 | Doken et al. | |
| 2014/0341056 A1 | 11/2014 | Carbajal | |
| 2014/0342836 A1 | 11/2014 | Pearce | |
| 2014/0343438 A1* | 11/2014 | Sweeney ............ A61B 5/4818 600/483 |
| 2014/0347491 A1 | 11/2014 | Connor | |
| 2014/0349256 A1 | 11/2014 | Connor | |
| 2014/0349257 A1 | 11/2014 | Connor | |
| 2014/0372250 A1 | 12/2014 | Dugan | |
| 2014/0378777 A1 | 12/2014 | Conrad et al. | |
| 2014/0378794 A1 | 12/2014 | Conrad et al. | |
| 2015/0039239 A1 | 2/2015 | Shuler et al. | |
| 2015/0046526 A1 | 2/2015 | Bush | |
| 2015/0101053 A1 | 4/2015 | Sipple | |
| 2015/0126873 A1 | 5/2015 | Connor | |
| 2015/0148621 A1* | 5/2015 | Sier ................ A61B 5/372 600/595 |
| 2015/0161738 A1 | 6/2015 | Stempora | |
| 2015/0164349 A1 | 6/2015 | Gopalakrishnan et al. | |
| 2015/0168365 A1 | 6/2015 | Connor | |
| 2015/0170504 A1 | 6/2015 | Jooste | |
| 2015/0178282 A1 | 6/2015 | Gorur et al. | |
| 2015/0199493 A1 | 7/2015 | Glenn et al. | |
| 2015/0220109 A1 | 8/2015 | von Badinski et al. | |
| 2015/0238125 A1 | 8/2015 | Acosta et al. | |
| 2015/0264459 A1* | 9/2015 | Luna ................ F21V 33/0056 381/386 |
| 2015/0294440 A1* | 10/2015 | Roberts ................ G06T 3/40 345/666 |
| 2015/0313489 A1 | 11/2015 | Bulkes et al. | |
| 2015/0324564 A1 | 11/2015 | Sahu et al. | |
| 2015/0352406 A1* | 12/2015 | Burich ................ G16H 40/67 700/91 |
| 2015/0359490 A1* | 12/2015 | Massey ............ A61B 5/4839 600/300 |
| 2015/0370994 A1* | 12/2015 | Madan ................ G16H 15/00 705/3 |
| 2016/0007899 A1* | 1/2016 | Durkee ................ G09B 23/28 600/300 |
| 2016/0012055 A1 | 1/2016 | Bai et al. | |
| 2016/0015275 A1 | 1/2016 | Samadani et al. | |
| 2016/0019813 A1 | 1/2016 | Mullen | |
| 2016/0034696 A1 | 2/2016 | Jooste et al. | |
| 2016/0058133 A1 | 3/2016 | Fournier | |
| 2016/0087976 A1 | 3/2016 | Kaplan et al. | |
| 2016/0113551 A1 | 4/2016 | Annegam et al. | |
| 2016/0128644 A1 | 5/2016 | Meier et al. | |
| 2016/0152180 A1 | 6/2016 | Kirsch et al. | |
| 2016/0165663 A1 | 6/2016 | Shanmugam et al. | |
| 2016/0178904 A1* | 6/2016 | Deleeuw ............ H04N 13/366 345/8 |
| 2016/0306945 A1 | 10/2016 | Jiang | |
| 2016/0345891 A1 | 12/2016 | Kirby et al. | |
| 2016/0379476 A1 | 12/2016 | Sella | |
| 2017/0007183 A1 | 1/2017 | Dusan et al. | |
| 2017/0039339 A1* | 2/2017 | Bitran ................ G16H 50/30 |
| 2017/0091421 A1* | 3/2017 | Kumar ................ G16H 20/00 |
| 2017/0216669 A1* | 8/2017 | Burich ................ G16H 40/63 |
| 2017/0227375 A1* | 8/2017 | Parikh ................ G01C 22/006 |
| 2017/0301214 A1* | 10/2017 | Chen ................ A61B 5/1112 |
| 2018/0193697 A1* | 7/2018 | Burich ................ G16H 40/67 |
| 2019/0156296 A1* | 5/2019 | Lu ................ A61B 5/024 |
| 2020/0118665 A1* | 4/2020 | Bender ................ G16H 50/30 |
| 2020/0121988 A1 | 4/2020 | Burich et al. | |
| 2020/0195599 A1* | 6/2020 | Ganesh ............ H04M 1/72451 |
| 2020/0219616 A1* | 7/2020 | Swift ................ G06N 3/08 |

(56) References Cited

U.S. PATENT DOCUMENTS

| | | | |
|---|---|---|---|
| 2020/0381095 A1* | 12/2020 | Li | G16H 50/30 |
| 2021/0106241 A1* | 4/2021 | Kerman | A61B 5/7267 |
| 2021/0200852 A1* | 7/2021 | Gupta | G06F 21/33 |
| 2021/0282686 A1* | 9/2021 | Chaturvedi | G06N 3/08 |

* cited by examiner

BASELINING USER PROFILES FROM PORTABLE DEVICE INFORMATION

RELATED APPLICATIONS

This application is a continuation of U.S. patent application Ser. No. 16/445,017, filed Jun. 18, 2019, which is a continuation of U.S. patent application Ser. No. 14/981,246, filed Dec. 28, 2015, which claims the benefit of U.S. Provisional Application No. 62/117,282, filed Feb. 17, 2015, and of U.S. Provisional Application No. 62/192,998, filed Jul. 15, 2015, the entire contents of which are incorporated by this reference.

BACKGROUND

As portable devices and technology continue to expand and develop individuals are increasingly searching for devices to measure and monitor various aspects of their lives. For example, wearable fitness monitors may enable users to measure how many steps an individual has taken over a period of time or an amount of time the individual may be active over a period of time. Smart watches may enable users to execute applications, receive and send text messages, make phone calls, and so forth. Portable medical devices may enable a user to take medical measurements outside of a hospital environment. For example, a diabetic may use a portable insulin measurement device to monitor their blood sugar level. While portable measurement and monitoring devices may provide users with rudimentary measurement and monitoring information, the portable measurement and monitoring devices fail to provide users with meaningful information to enable users to analyze and improve many desired aspects of their lives.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure in which like components may be labeled with corresponding numbering; and, wherein.

Figure 1:
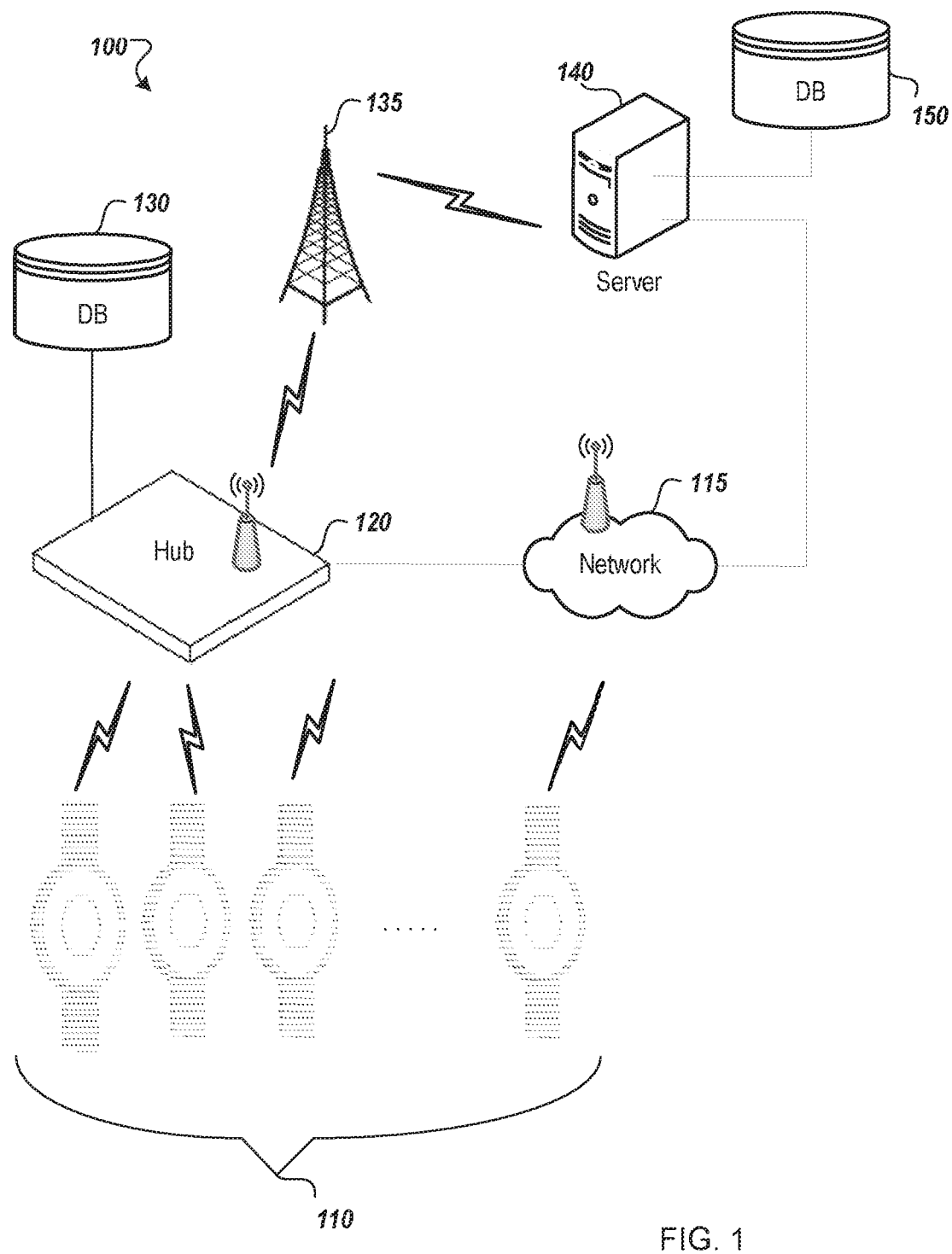
FIG. 1 is a block diagram of a system for measurement correlation, information tracking and setting baselines for users of user measurement devices (UMDs) according to one embodiment.

Reference will now be made to the exemplary embodiments illustrated, and specific language will be used herein to describe the same. It will nevertheless be understood that no limitation of the scope of the invention is thereby intended.

DETAILED DESCRIPTION

As data becomes increasingly easier to access, individuals increasingly desire to monitor, collect, and/or analyze various aspects of their environment and/or physiology.

For example, a sport or fitness enthusiast may desire to monitor, collect, and/or analyze various aspects of the fitness routine (such as their heart rate, workout intensity, workout duration, and so forth) to determine how to improve and adjust their fitness routine to increase its efficacy. In another example, an asthmatic may desire to monitor, collect, and/or analyze environmental condition information (such as air quality, pollen count, and so forth) to determine and avoid conditions that may aggravate their condition. However, traditional portable devices or wearable devices provide users with limited and incomplete information to monitor, collect, and/or analyze environment or physiology information desired by the user.

Aspects of the present disclosure address the above-noted deficiency by using a user monitoring system to monitor, collect, and/or analyze physiological and environmental data and information. The user monitoring system may include a user measurement device (UMD) to monitor, collect, and/or analyze desired environmental and/or physiological aspects of the user and the user's environment. The UMD may use sensors, stored data, real-time data, received data, and/or algorithms to monitor, collect, and/or analyze environmental and/or physiological information related to an individual, a group of individuals, or a business.

In one embodiment, a UMD may include a housing formed and shaped to affix to a user to engage a body. A sensor integrated into the housing can take physiological measurements of the user to obtain first physiological data and second physiological data. A processing device located within the housing (or elsewhere, as in a server device) may receive the first physiological data and the second physiological data. The processing device may analyze the first physiological data to determine a first correlation between the first physiological data and a physiological parameter and analyze the second physiological data to determine a second correlation between the second physiological data and the physiological parameter. The processing device may then predict a change in the level of the physiological parameter according to a combination of the first correlation and the second correlation. In one example, the first physiological data may include optical spectroscopy levels, the second physiological data may include skin impedance levels, and the physiological parameter may be hydration, although other combinations of envisioned as will be discussed. The sensor may be a part of a sensor array including multiple individual sensors.

In another, or related, embodiment an apparatus may include a processing device and non-transitory computer-readable medium storing instructions and data. The processing device may execute the instructions to perform a series of functions. In one embodiment, the processing device may receive sensor data including physiological data and environmental data. The processing device may further analyze historical physiological data and environmental data to determine a first correlation between a first physiological parameter and a second physiological parameter and a second correlation between an environmental parameter and the second physiological parameter. The processing device may then predict a change in a level of the second physiological parameter of an identified person for which the physiological data is received based on the first correlation and the second correlation.

In one embodiment, the first physiological parameter may be any or a combination of oxygenation, heart rate, skin temperature, optical spectroscopy (or tissue blood volume reflection and absorption), bio-impedance spectroscopy, and blood pressure, for example. The tissue-blood volume reflection and absorption level may also be referred to as tissue bulk absorption level for ease of explanation. The second physiological parameter may be hydration or oxygenation. The environmental data may be any or a combination of ambient temperature, ambient humidity, altitude, geographical location, and time of day, by way of example. The historical physiological data may be of the identified person or of a group of persons.

In another, or related, embodiment a method may include receiving, during a first period, first physiological data and second physiological data from a sensor engaging a body of a user. The method may further include analyzing, using at least one processing device, the first physiological data to determine a first correlation between the first physiological data and a physiological parameter and analyzing the second physiological data to determine a second correlation between the second physiological data and the physiological parameter. The method may further include predicting a change in a level of the physiological parameter during a second time period according to a combination of the first correlation and the second correlation, wherein the first physiological data and the second physiological data may exclude the physiological parameter to which the correlation is being made. Only by way of example, the first physiological data may include an average tissue bulk absorption, the second physiological data may include an average bio-impedance spectroscopy, and where the physiological parameter may be hydration. In this example, when the average tissue bulk absorption decreases and the average skin impedance increase, the processing device may predict that the hydration level of the user may decrease (e.g., the user is becoming dehydrated).

FIG. 1 is a block diagram of a system 100 for measurement correlation, information tracking and setting baselines for users of user measurement devices (UMDs). The system 100 may include a plurality of UMDs 110 of different users, for instance of a group of users such as athletes that compete separately and/or athletes on the same team or that compete in the same or similar sport. The system 100 may further include a communications network 115 over which the UMDs communicate with a hub 120 (or base station) and a server 140. The system 100 may include a tower 135 such as a cellular tower or other wireless (and/or wired) access source for communication between the hub 120 and the server 140.

The hub 120 may include memory and storage with a database 130 for storing measurement, environmental and baseline data of the users. The server 140, which may be cloud-based, may also include memory and storage to include a database 150 for storing measurement, environmental and baseline data of the users. Processing to execute measurement correlation, information tracking and setting of baselines for physiological parameters may occur within the UMDs 110, within the hub 120 and/or within the server 140, in various embodiments of the present disclosure as will be explained in more detail.

Figure 2A:
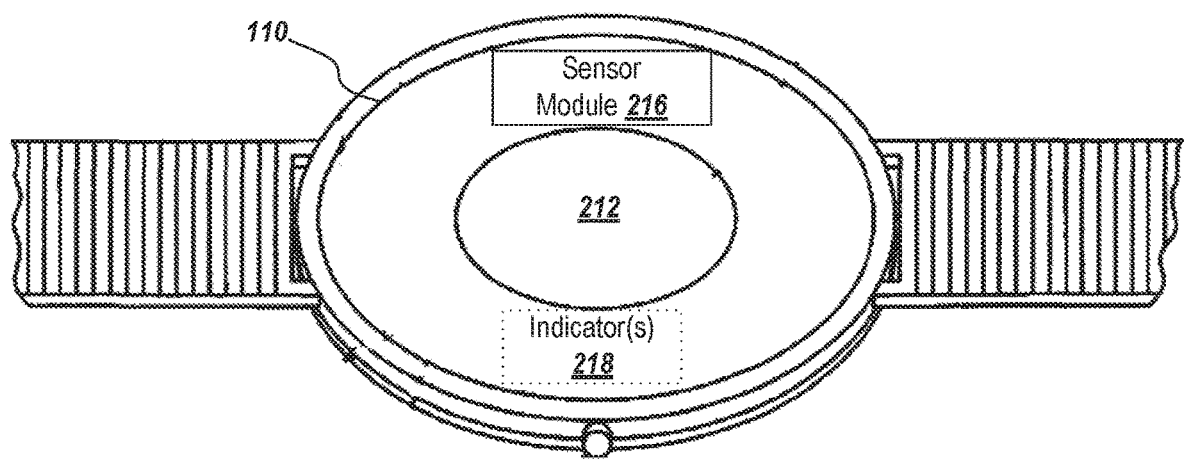
FIG. 2A illustrates a bottom view of the user measurement device (UMD), such as a wearable wristband, that may be used to take measurements using one or more sensors according to one embodiment.

FIG. 2A illustrates a bottom view of the UMD 110, such as a wearable wristband, that may be used to take selected measurements using one or more sensors 212 and a sensor module 216, according to one embodiment. The UMD 110 may also include one or more indicators 218 used to alert the user of the UMD to adjust hydration, activity levels, or take specific actions in preparation of an anticipated physical activity. The indicators 218 may be on the top or the bottom of the UMD depending on the type of indicator, such as a display or light may be on the top and a vibrator may be on the bottom of the UMD. The UMD may also be a non-invasive device, such as another banded device such as a headband, an armband, a leg band, an invasive device, or another type of device attachable to (or implantable within) a body of a user to obtain physiological measurements from the user.

In one embodiment, the one or more sensors 212 may be a bio-impedance or a bioimpedance spectroscopy sensor, an accelerometer, a three dimensional (3D) accelerometer, a gyroscope, a light sensor, an optical sensor, an optical spectroscopy sensor, a heart rate monitor, a blood pressure sensor, a pulse oximeter, and so forth. The sensor module 216 may receive measurement information from the one or more sensors 212 and analyze the measurement information to determine selected physiological information and/or medical information, such as a hydration level of the user, cardiac information of the user (e.g., blood pressure or heart rate), a blood oxygen level of the user, a tissue bulk absorption and so forth.

Figure 2B:
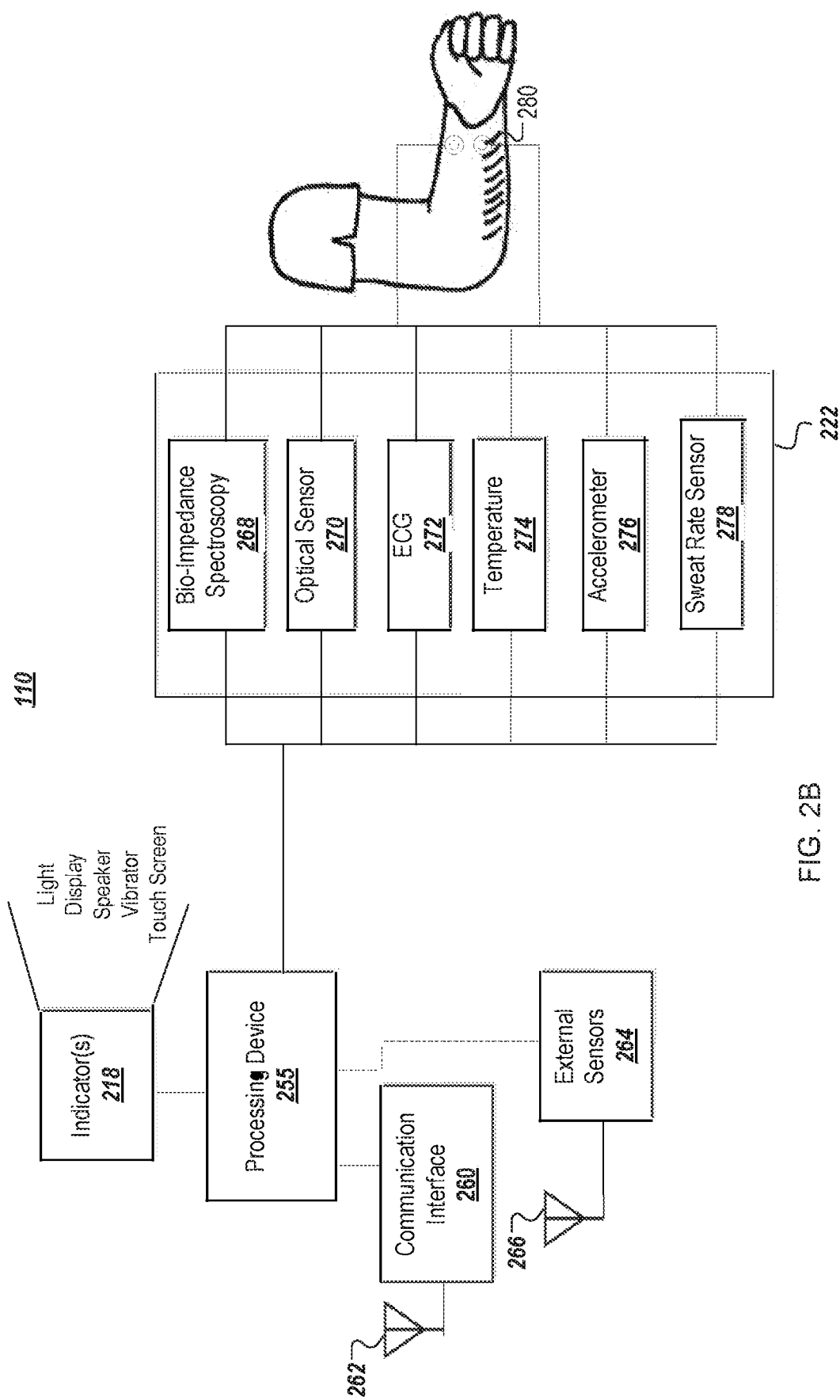
FIG. 2B illustrates a schematic view of the UMD according to one embodiment.

FIG. 2B illustrates a schematic view of the UMD 110 according to one embodiment. The UMD 110 may include the indicators 218, a sensor array 222 (to include at least the sensor 212 as in FIG. 2A), a processing device 255, a communications interface 260, an antenna 262 coupled with the communications interface 260, external sensors 264, and accompanying antenna(s) 266. In one example, the sensor array 222 may include one or more physiological sensors to take physiological measurements (e.g., measurements related to the body of the individual or animal). The sensor array 222 may include one or more sensors to engage a user of the UMD to take measurements. In various examples, the sensor array 222 may include, without limitation: a bio-impedance spectroscopy sensor 268 (or simply impedance sensor 268), an optical sensor 270, an electrocardiogram (ECG) sensor 272, a temperature sensor 274 (such as a thermostat or thermistor), an accelerometer 276, a sweat rate sensor 278 and so forth. The temperature sensor 274 may measure a temperature of the skin, of a core temperature of a user, or both. The sweat rate sensor 278 may measure a rate at which a user perspires to lose sweat.

Figure 2C:
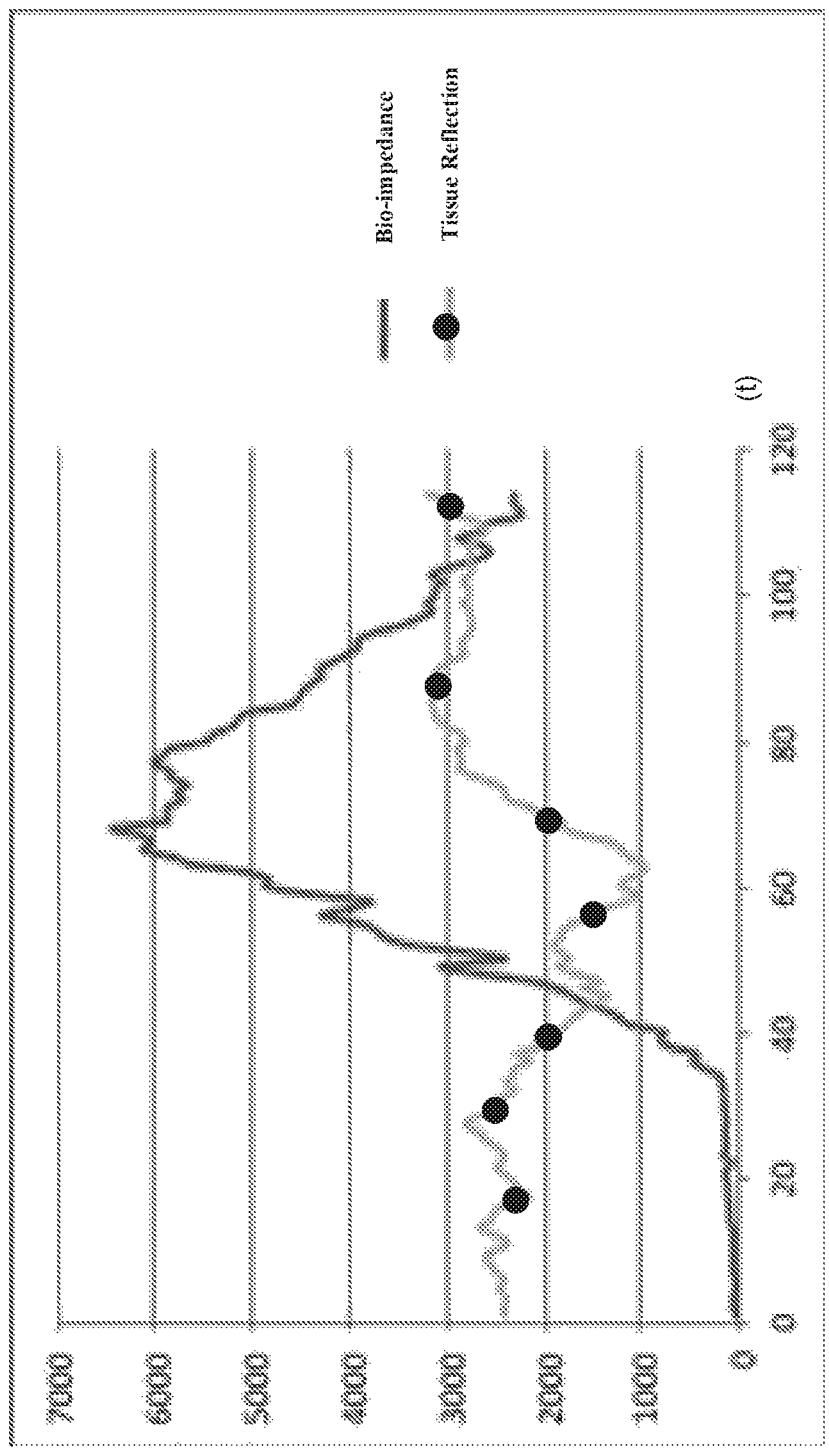
FIG. 2C illustrates a graph correlating bio-impedance spectroscopy with tissue blood volume reflection and absorption (or tissue bulk absorption) of an individual that becomes dehydrated mid-way through a workout.

With reference to FIG. 2C, bio-impedance (shown as the y-axis), when measured by the bio-impedance spectroscopy sensor 268, may determine the electrical impedance or opposition to the flow of an electric current through body tissues at a range of frequencies. This is to be distinguished from doing a simple bio-impedance measurement at one or a few discrete frequencies, which would not yield the abundance of information available from a full spectrum sweep that the bio-impedance spectroscopy sensor 268 performs. This (full spectrum) impedance may then be used to calculate an estimate of total body water (TBW) of an individual, which in turn may be used to estimate fat-free body mass, and by difference with body weight, body fat of the individual. As used herein, bio-impedance generally refers to electrical impedance by virtue of TBW as measured through the skin, which may be correlated with hydration and other physiological parameters.

Furthermore, the optical sensor 270 may perform optical spectroscopy of a skin of an individual wearing the UMD 110. This optical spectroscopy may also be referred to as tissue blood volume reflection and absorption (or more simply as tissue bulk absorption) as being a test of how much light, when directed at the skin, is absorbed compared to how much is reflected and in what wavelengths of the light spectrum. For example, tissue bulk absorption generally refers to a brightness of a light source of a certain wavelength as it appears to the eye, measured as a ratio of luminous flux to radiant flux at that wavelength. The skin may include blood, collagen, and other compounds being tested by the optical spectroscopy. When the skin is tested as that light source in response to light from the optical sensor 270, the optical sensor may detect how much light is being reflected as a volume reflection and absorption parameter. When most of the light is absorbed, tissue bulk absorption is high, which may occur when an individual is dehydrated.

For example, as shown in the middle of the graph in FIG. 2C, as bio-impedance spectroscopy goes up over time (such as during exercise), the tissue reflection level detected from the optical sensor goes down, e.g., the tissue bulk absorption increases. In other words, bioimpedance spectroscopy and tissue reflection level are inversely correlated with respect to hydration, e.g., bio-impedance goes up and tissue reflection level goes down as a level of hydration decreases. And, similarly, as the individual cools down and/or hydrates, the bioimpedance level comes back down and the tissue reflection level goes back up (and tissue bulk absorption decreases), as seen at the right-most part of the graph in FIG. 2C.

With reference to the other sensors of the sensor array 222, one could also expect skin temperature to increase as hydration decreases due to the body's inability to cool itself as dehydration sets in. Furthermore, the individual's heart rate may also increase as dehydration puts stress on the body. In this way, the data from the different sensors of the sensor array 222 may inter-correlate and may do so in ways that generalize over a population at higher granularities, and may do so in ways that are more customized to individuals at lower granularities.

With further reference to FIG. 2B, the processing device 255 may include a processor, a memory storage device, an analog-to-digital converter, and/or a digital-to-analog converter. In one example, the processing device 255 may be coupled to the communication interface 260 to communicate data with other devices using the antenna 262. The antenna 262 may be configured to communicate on a wireless network and/or a cellular network such as the communications network 115 (see FIG. 14). In another example, the processing device 255 may be coupled to one or more external sensors. The external sensors 264 may be sensors that take measurements external to the user, such as non-physiological measurements or non-direct engagement measurements of the user, including environmental parameters, temperature, humidity, altitude, wind and the like. The external sensors 264 may include, or be integrated with, a global positioning system (GPS) device, a triangulation device, a humidity sensor, an altimeter, and so forth.

In other embodiments, the processing device 255 or a portion of the processing device 255 may be located elsewhere such as in the hub 120 (or base station), a communication switch or a server 140, for example. Such examples will be discussed in more detail with reference to FIG. 4.

Figure 3:
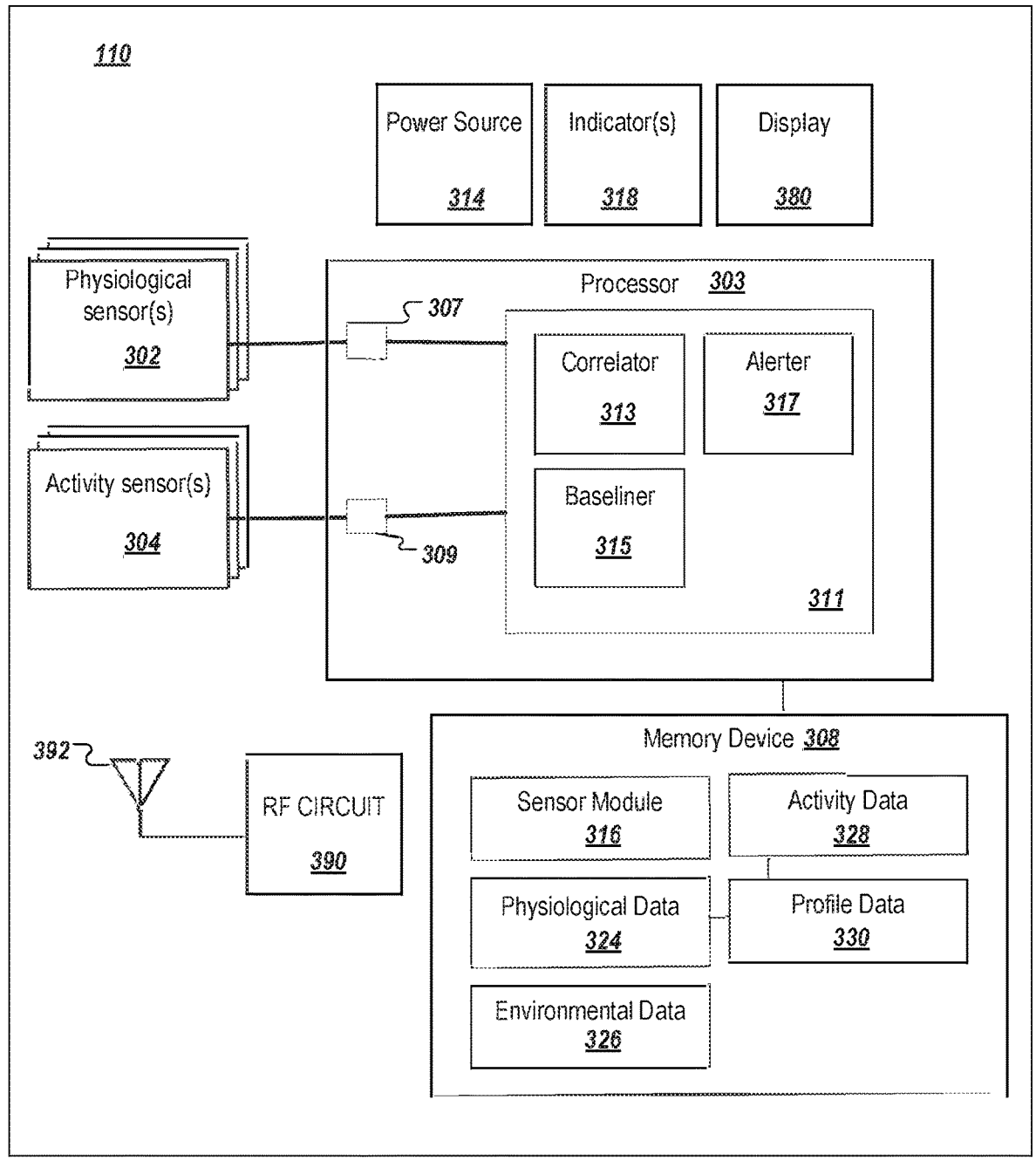
FIG. 3 is a block diagram of a wearable UMD with a correlator, a baseliner, and an alerter according to one embodiment.

FIG. 3 is a block diagram of the wearable UMD 110 with a correlator, a baseliner, and an alerter according to one embodiment. The wearable UMD 110 may include, without limitation, one or more physiological sensor(s) 302, one or more activity sensor(s) 304, a processor 303, a memory device 308, a display 380, a radio frequency (RF) circuit 390 and an antenna 392 coupled to the RF circuit 390. The RF circuit 390 may communicate with the communications network 115, the hub 120 and optionally with other wireless devices such as UMDs 110 of other users, as shown in FIG. 1.

The processor 303 may include a first sensor interface 307 for receiving sensor data from the physiological sensor(s) 302, a second sensor interface 309 for receiving sensor data from the activity sensor(s) 304, and a processing component 311. The processing component 311 in turn may include a correlator 313, a baseliner 315 and/or an alerter 317. The memory device 308 may further include, without limitation, a sensor module 316, physiological data 324, environmental data 326, activity data 328 and profile data 330.

The wearable UMD 110 may include the sensor array 222 (FIG. 2B) with two or more sensors. In the depicted embodiment, the wearable UMD 110 may include one or more physiological sensors 302 and one or more activity sensors 304. In some instances, the activity sensors 304 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph). Physiological measurements may also include motion and/or movement of the body. In some cases, these physiological measurements may be taken as an aggregate, e.g., as physiological data, with which to correlate to other physiological measurements, a physiological parameter, and/or an environmental parameter.

Herein, a parameter may generally be considered a measurable quantity (such as heart rate, tissue-blood volume reflection and absorption, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 302 may include a pulse oximeter sensor, an electrocardiography (ECG) sensor, a fluid level sensor, an oxygen saturation sensor, a body temperature sensor (e.g., a skin temperature sensor), a skin temperature sensor, a plethysmograph sensor, a respiration sensor, a breath sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor.

The activity sensors 304 may be any of the physiological sensors described above, but in some cases, the activity sensors 304 are Newtonian sensors, such as, for example, a gyroscope sensor, a vibration sensor, an accelerometer sensor (e.g., a sensor that measures acceleration and de-acceleration), a three dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 302 may be used for specific physiological measurements.

In another embodiment, the physiological sensors 302 and activity sensors 304 may be categorized into physiological sensors, environmental sensors, and Newtonian sensors. The one or more physiological sensors may be a pulse oximeter sensor, an electrocardiography (ECG) sensor, a fluid level sensor, an oxygen saturation sensor, a body temperature sensor, an ambient temperature sensor, a plethysmograph sensor, a respiration sensor, a breath sensor, a cardiac sensor, a heart rate sensor, an impedance sensor, an optical sensor, a spectrographic sensor, or the like. The one or more environmental sensors may be, for example, a humidity sensor, an ambient temperature sensor, an altitude sensor, a barometer, a global positioning system (GPS) sensor, a triangulation sensor, a location sensor, or the like. The one or more Newtonian sensors may be, for example, a gyroscope sensor, a vibration sensor, an accelerometer sensor, a three dimensional (3D) accelerometer sensor, a force sensor, a pedometer, a strain gauge, a magnetometer, a geomagnetic field sensor, or the like. Alternatively, other types of sensors may be used to measure physiological measurements, including measurements to determine activity levels of a person wearing the UMD. Furthermore, environmental data may be obtained from other sources such as through the network 115 from sources reachable in the cloud or online.

The first sensor interface 307 may be coupled with the one or more physiological sensors 302 and a second sensor interface 309 may be coupled with the one or more activity sensors 304. The processing component 311 may be operable to execute one or more instructions stored in the memory device 308, which may be coupled with the processor 303. In some cases, the processing component 311 and memory device 308 may be located on a common substrate or on a same integrated circuit die. Alternatively, the components described herein may be integrated into one or more integrated circuits as would be appreciated by one having the benefit of this disclosure. The memory device 308 may be any type of memory device, including non-volatile memory, volatile memory, or the like. Although not separately illustrated, the memory device may be one or more types of memory configured in various types of memory hierarchies.

The memory device 308 may store physiological data 324, such as current and past physiological measurements, as well as profile data 330, including user profile data, bibliographic data, demographic data, and the like. The physiological data 324, and in some cases the profile data 330, may also include processed data regarding the measurements, such as statistical information regarding the measurements, as well as data derived from the measurements, such as predictive indicators, results, and/or recommendations.

The profile data 330 may also include information connected to user profiles of the users that wear the UMDs 110, such as gender, age, weight, health, fitness level, and family health histories. The profile data 330 may also be linked to various physiological data 324 and activity data 328 and tracked over time for the users. The profile data 330 may further include baselines of physiological parameters for respective users. In one example, the baselines are of a heart rate, blood pressure, bio-impedance spectroscopy, skin temperature, tissue bulk absorption, oxygen levels, hydration levels, electrolyte levels and so forth. When the baselines are included with the user profiles, the user profiles may be referred to as baseline profiles for the respective users.

The memory device 308 may also store activity data 328. The activity data 328 may be current and past measurements, as well as predictive data for predictive modeling of activity levels. The memory device 308 may store instructions of the sensor module 316 and instructions and data related to the correlator 313, the baseliner 315 and the alerter 317, which perform various operations described below.

In particular, the sensor module 316 may perform operations to control the physiological sensors 302 and activity sensors 304, such as when to turn them on and off, when to take a measurement, how many measurements to take, how often to perform measurements, etc. For example, the sensor module 316 may be programmed to measure a set of physiological measurements according to a default pattern or other adaptive patterns to adjust when and how often to take certain types of measurements. The measurements may be stored as the physiological data 324, the environmental data 326, and the activity data 328, and some of them may also be integrated as a part of the profile data 330, as discussed.

In the depicted embodiment, the processing element 303 (e.g., one or more processor cores, a digital signal processor, or the like) executes the instructions of the sensor module 316 and those related to the correlator 313, the baseliner 315, the alerter 317 and possibly other modules or routines. Alternatively, the operations of the sensor module 316 and the correlator 313, the baseliner 315 and the alerter 317 may be integrated into an operating system that is executed by the processor 303. In one embodiment, the processing component 311 measures a physiological measurement via the first sensor interface 307. The processing component 311 may measure an amount of activity of the wearable UMD 110 via the second sensor interface 309. The amount of activity could be movement or motion of the wearable UMD 110 (e.g., by tracking location), as well as other measurements indicative of the activity level of a user, such as heart rate, body temperature, tissue bulk absorption, or the like.

In one embodiment, the activity sensors 304 may include a hardware motion sensor to measure at least one of movement or motion of the wearable UMD 110. The processing component 311 may determine the amount of activity based on the movement or motion of the wearable UMD 110. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 303 may further execute instructions to facilitate operations of the UMD 110 that receive, store and analyze measurement data, environmental data and profile data. The indicator(s) 318 may include one or more of a light, a display, a speaker, a vibrator, and a touch display, useable to alert the user to take actions in response to trending levels of physiological parameters during or after physical activity and/or prepare for undertaking anticipated physical activity.

In some embodiments, for example, the correlator 313 may analyze measurement data to correlate physiological data and/or environmental data with a physiological parameter of interest (such as hydration or oxygenation) in order to predict a change in a level of the physiological parameter of interest. Such prediction may enable timely and accurate recommendations to a user in terms of hydrating, adjusting effort levels or other specific actions to address a trend or a change in the physiological parameter. The recommendations may be displayed in the display 380, sent via an alert through one of the indicator(s) 318 or displayed in another device such as a smartphone or tablet or other computing device.

In another embodiment, the correlator 313 may also track and analyze activity data of the user related to physiological or determined parameters (such as heart rate, oxygenation, tissue bulk absorption, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the UMD 110 may track activity data over time, intelligently and continuously (or periodically) analyze all of this information, and alert the user through the indicator(s) 318 to take a specific action at a proper time before a start of the physical activity, as will be explained in more detail. The proper time may include to hydrate extra in the hours before physical activity and to eat at least two hours before any physical activity, or other such timing that may be general to most users, or customized to a training or nutrition routine of a specific user.

The alerter 317 may decide the most appropriate timing and mode of alert, whether through one of the indicator(s) 318, the display 380 or another device such as a smartphone, tablet or the like. The type of indicator used to alert the user may also be customized to or by the user.

In one embodiment, the correlator 313 may determine a correlation between different data points or data sets of the input data (such as data collected from different sensors, devices, or obtained from the cloud or online). The correlator 313 may determine different types of correlations of the data points or data sets. In one example, the correlator 313 may execute a Pearson product moment correlation coefficient algorithm to measure the extent to which two variables of input data may be related. In another example, the correlator 313 may determine relations between variables of input data based on a similarity of rankings of different data points. In another example, the correlator 313 may use a multiple regression algorithm to determine a correlation between a data set or a data point that may be defined as a dependent variable and one or more other data sets or other data points defined as independent variables. In another example, the correlator 313 may determine a correlation between different categories or information types in the input data.

In further examples, when the correlator 313 determines a correlation between the different data points or data sets, the correlator 313 may use the correlation information to predict when a first event or condition may occur based on a second event or condition occurring. In another example, when the correlator 313 determines a correlation between the different data points or data sets, the correlator 313 may use the correlation information to determine a diagnosis or result data. In another example, when the correlator 313 determines a correlation between the different data points or data sets, the correlator 313 may use the correlation information to determine a cause of a condition and/or event.

Additionally, or alternatively, the correlator 313 may determine a correlation between physiological data and environmental data. For example, the input data may include hydration level data (physiological data) and ambient temperature data (environmental data). In this example, the correlator 313 may identify a correlation between when the ambient temperature increases and a decrease in a hydration level of a user. The correlator 313 may identify the correlation between the ambient temperature and the hydration level by using a regression algorithm with the ambient temperature as an independent variable and the hydration level as a dependent variable. When the correlator 313 has identified the correlation between the ambient temperature and the hydration level, the correlator 313 may predict a change in a hydration level of a user or a rate of change of a hydration level of a user based on the ambient temperature.

Additionally, or alternatively, the correlator 313 may determine a correlation between an altitude level and an oxygenation level of a user. For example, the correlator 313 may determine a correlation between an increase in the altitude level and a decrease in the oxygenation level of the user. When the correlator 313 determines the correlation between the altitude level and the oxygenation level, the correlator 313 may predict a change in the oxygenation level of the user based on the altitude level at which the user is currently.

The preceding examples are intended for purposes of illustration and are not intended to be limiting. The correlator 313 may identify a correlation between various data points, data sets, and/or data types. After having a correlation that informs, for example, the hydration level and/or oxygenation level of the user, and further in consideration of a present activity level of the user, the alerter 317 may alert the user at the proper time when to hydrate or how to moderate activity levels for healthy functioning of the body and its organs, or for maximizing performance of an athlete.

In a further example, the correlator 313 may identify a correlation between location information and physiological data of a user. For example, the correlator 313 may determine a location of a user for at a period of time, such as by using GPS sensor data or triangulation sensor data. In this example, the correlator 313 may receive physiological measurement data (such as heart rate measurement data, optical spectroscopy data, hydration level measurement data, blood pressure measurement data, and so forth). The correlator 313 may correlate the location of the user with the physiological measurement data to increase an accuracy of data analysis, a diagnosis, or result data and/or provide additional details regarding a cause of physiological measurements or trends.

In one example, the correlator 313 may determine that a user is at work in an office location. When the correlator 313 detects an increase in a heart rate or a blood pressure of a user, the correlator 313 may correlate heart rate or blood pressure data with the location information to determine a cause of the increase in heart rate or blood pressure. For example, when a heart rate or blood pressure of an individual increases while at a work in an office, the correlator 313 may determine that the heart rate or blood pressure increase may be due to psychological causes (such as stress) rather than physiological causes (such as exercising or working out) because the user is at a location where an individual is not likely to physically exert himself or herself.

In a further example, the correlator 313 may use a multiple regression algorithm to determine a correlation between multiple physiological and/or environmental data points or data sets. For example, the correlator 313 may receive heart rate data, skin temperature, bioimpedance spectroscopy data, tissue bulk absorption, and hydration level data of a user. In this example, the correlator 313 may determine a correlation between these types of physiological data and a hydration level of the individual. For example, the physiological data could be from optical spectroscopy (tissue-blood volume reflection and absorption, or more simply, tissue bulk absorption) and/or bio-impedance spectroscopy data. The correlator 313 may then determine that as the bio-impedance of an individual increases and tissue bulk absorption decreases, the hydration level of the individual may decrease.

Additionally, or alternatively, the correlator 313 may filter out a correlation determination (e.g., a determination that data points or data sets may be correlated) when a correlation level is below a threshold level. For example, when the correlator 313 determines that there may be a 30 percent correlation between a skin temperature or a bio-impedance spectroscopy level of an individual and a hydration level of an individual, the correlator 313 may filter out or disregard the correlation information when determining a cause of a condition or event, a result of the data, or a diagnosis or prediction.

Additionally, or alternatively, the correlator 313 may discount or weight a correlation determination based on the correlation level of the correlation determination. For example, when the correlator 313 determines that there may only be a 30 percent correlation between a bioimpedance level of an individual and a hydration level of an individual, the correlator 313 may discount or assign a lower weight to the correlation determination (relative to a higher correlation percentage such as 90 percent) when determining a cause of a condition or event, a result of the data, or a diagnosis.

Additionally, or alternatively, the correlator 313 may assign weights to different factors, such as physiological data (e.g., different types or qualities of physiological parameters), environmental data (e.g., different types or quality of environmental parameters), time of day, and so forth. Quality of data may reference a signal-to-noise (SNR) ratio of that data, where the higher the SNR, the higher the weight may be applied to the data. In regards to data type, in one example, the correlator 313 may assign a first weight to hydration level data of an individual and a second weight to heart rate data of an individual when determining a performance level of an individual. In this example, when determining a performance level, the correlator 313 may assign a higher weight to the hydration level data relative to the heart rate data, for example.

The correlator 313 may additionally, or alternatively, use predetermined weights for the different physiological and/or environmental data. In another example, the correlator 313 may receive user-defined or predefined weights from an input device indicating the weights for the different physiological and/or environmental data. In another example, the correlator 313 may determine the weights to assign to the different physiological and/or environmental data based on correlation levels of the different physiological and/or environmental data. For example, when a correlation level between a humidity level and a heart rate of an individual may be relatively low over a threshold period of time and/or under a threshold number of different conditions, the correlator 313 may assign a low weight to humidity level data when determining a cause of a change in heart rate of a user.

In one example, the correlator 313 may assign different weights to physiological measurements based on environmental data. For example, based on a location of an individual, the correlator 313 may assign a first weight to a heart rate measurement and a second weight to a respiration sensor measurement.

In another example, the correlator 313 may assign weights to different causes, diagnosis, or results, such as an exertion level (e.g., working out or sleeping), a stress level, an amount of time a user sleeps each day, and so forth.

Additionally, or alternatively, the correlator 313 may use environmental data to determine a cause of a physiological diagnosis. For example, when a user is located at a fitness facility working out, the correlator 313 may increase a weight for physical exertion diagnosis as a cause of physiological measurements (such as an increase in a heart rate or decrease in a hydration level of a user). In another example, when a user is located at home in bed resting or sleeping, the correlator 313 may correlate a location of the user with physiological measurements of the user. In this example, the correlator 313 may determine that a decrease in heart rate may be due to an individual going to sleep when a user is located in their bedroom for a threshold period of time.

The correlator 313 may further combine environmental data used in this way with a correlation determination between a physiological parameter and physiological data such as past measurements of the user or of a group of users.

The correlator 313 may track, sort and/or filter input data. The input data may include user schedule information, such as a daily schedule of the user; survey information, such as information received from surveys of individuals; research information, such as clinical research information or academic research information associated with one or more measurements of the UMD; and so forth.

The correlator 313 may use location-based tracking and/or scheduling information of the user in determining an expected or probable activity of a user. For example, when a user is a member of a sports team, the user's schedule may include practice schedule information and/or game schedule information. In this example, the correlator 313 may use the schedule information to anticipate that the user may be participating in physical activity and the alerter 317 provide recommendations to the user based on the anticipated physical activity. For example, the correlator 313 may determine that the user may be practicing in two hours, may determine a current hydration level of the user, and may communicate a recommendation (such as via a sensory indicator of the UMD) to increase the hydration level of the user. A sensory indicator, such as one of the indicator(s) 318, may include: a visual indication device, such as a display; an auditory indication device, such as a speaker; and/or touch indication device, such as a vibrator.

In another example, the correlator 313 may use the scheduling information in correlation with a location of the user to determine an expected or probable activity. For example, the scheduling information may indicate that the user may be scheduled to attend a lecture at a physical fitness facility and the correlator 313 may adjust a location-based recommendation in view of the scheduling information. In this example, while the correlator 313 may typically recommend increasing a hydration level of the user in anticipation of physical activity based on the location information (e.g., the physical fitness facility), the correlator 313 may adjust the recommendation in view of the scheduling information that the user may be attending a lecture rather than working out.

Additionally, or alternatively, the correlator 313 may track and update activity levels of users and correlate these levels with locations of the users over time. For example, the GPS sensor of the UMD 110 may indicate that the user usually works out at the gym on Monday, Wednesday, and Friday at 7 a.m. and goes on a long bike ride on Saturday, usually starting about 8:30 a.m. Although these activities may not be available within the scheduling information or data of the UMD 110 (or other tethered device), the correlator 313 may execute machine learning to add to a user's activity data these events that normally occur.

Furthermore, the UMD 110 may distinguish the activity based on the analysis of the context of physiological measurements, environmental data, and user profile data. For example, the correlator 313 may determine that the user is at the gym on certain days because of the location of the gym, and may correlate an increase in heart rate with each visit, strengthening the probability that the user is working out at that gym location. Similarly, the GPS sensor of the correlator 313 may track the user's bike ride on Saturday and note 40-60 miles routes during periods of increased heart rate. The correlator 313 may exclude driving as the activity based on one or more factors, such as a speed of travel being far below that of the speed limit for automobiles and/or a skin impedance or temperature that is higher than when the user is driving. The correlator 313 may also track non-physical activity events such as periods of time the user normally sleeps, is at work, or is at leisure such as at a resort, fishing or on vacation. All of these activities may be learned and programmed into the UMD over time as part of the user's activity data.

The UMD 110 may store historical or previous input data of the user. In one example, the correlator 313 may store the historical information on the memory device 308 of the UMD 110. In another example, the correlator 313 may use the communication interface 260 (FIG. 2B) to store the information on a memory device coupled to or in communication with the UMD, such as a cloud-based storage device or a memory device of another computing device. In another example, the correlator 313 may be part of a cloud-based system or the other computing device, as will be discussed in more detail with reference to FIG. 4.

The correlator 313 may filter and/or sort input data. In one example, the correlator 313 may receive a filter or sort command from the UMD or an input device to filter and/or sort the input data. In another example, the filter or sort command may include filter parameters and/or sort parameters. The filter parameters and/or sort parameters may include a time of day, a day of the week, group information, individual information, a measurement type, a measurement duration, an activity type, profile information, injury information, performance level information, and so forth.

In another example, the correlator 313 may sort and/or filter the input data based on a trending of input data. For example, the correlator 313 may sort input data that may be trending in an increasing direction or a decreasing direction and may sort the input data based on the trending. In this example, different measurements for a user may be trending in different directions, such as a hydration level of a user may be trending towards a dehydrated level and an activity level of the user may be stable or stagnant. The correlator 313 may sort input data to display hydration level trending because the user may be trending towards dehydration while filtering out or disregarding the activity level information.

In one example, the correlator 313 may sort or filter the input data on a group level. In another example, the correlator 313 may sort or filter the input data on an individual level.

In another embodiment, the baseliner 315 may receive profile information from a new user to include any or a combination of gender, age, weight, health, fitness level, and family health histories. The health and fitness levels of the user may be based at least in part on physiological measurements received from the physiological sensor(s) 302 and the activity data received from the activity sensors 304. The baseliner 315 may then identify, from a plurality of baseline profiles of other users (e.g., a group of users), a baseline profile that is most similar to the user profile based on a correlation between the user profile information and baseline profile information. The baseliner 315 may then be able to set a baseline against which to judge measurements of a physiological parameter of the user that corresponds to levels of the physiological parameter of an individual with the baseline profile that is most similar. In an alternate embodiment, the baseline profile that is most similar to the user profile is identified from an aggregated baseline profile for a plurality of individuals corresponding to the plurality of baseline profiles.

Alternatively, or additionally, the most-similar profiles may look at physiological and/or environmental measurements of the individual as compared to the group. For example, the user may be most similar to another individual because they both react physiologically similarly to hot temperatures outside. In another example, the user may have a similar dehydration profile to the most-similar profile, meaning, when the user works out the user may reach a dehydration level at a certain point in time that substantially matches the timing of the most-similar profile.

The UMD 110 may further receive survey information and/or research information from an input device with which to build or add to the user and/or baseline profiles. For example, the UMD 110 may receive survey information that includes: gender information, age information, physical weight information, general health information, family information, fitness level information, and so forth. In one example, the correlator 313 may determine a correlation between the survey information and user input data. For example, the correlator 313 may correlate the age, weight, fitness level, and general health level of a user with survey information from other individuals to determine a correlation between the survey information for the individual and the other individuals. In this example, the baseliner 315 may set a baseline for a measurement of the UMD 110 for the individual based on baselines for the other individuals with the same or similar survey information.

In another example, the correlator 313 may correlate the user information with research information (such as research papers, clinical studies, and so forth). For example, the UMD may retrieve research information related to a physiological parameter, the correlator 313 may then correlate the research information with measurements of the physiological parameter of the user to generate a research correlation. The baseliner 315 may then adjust the baseline set for the user related to the physiological parameter in response to the research correlation.

Figure 4:
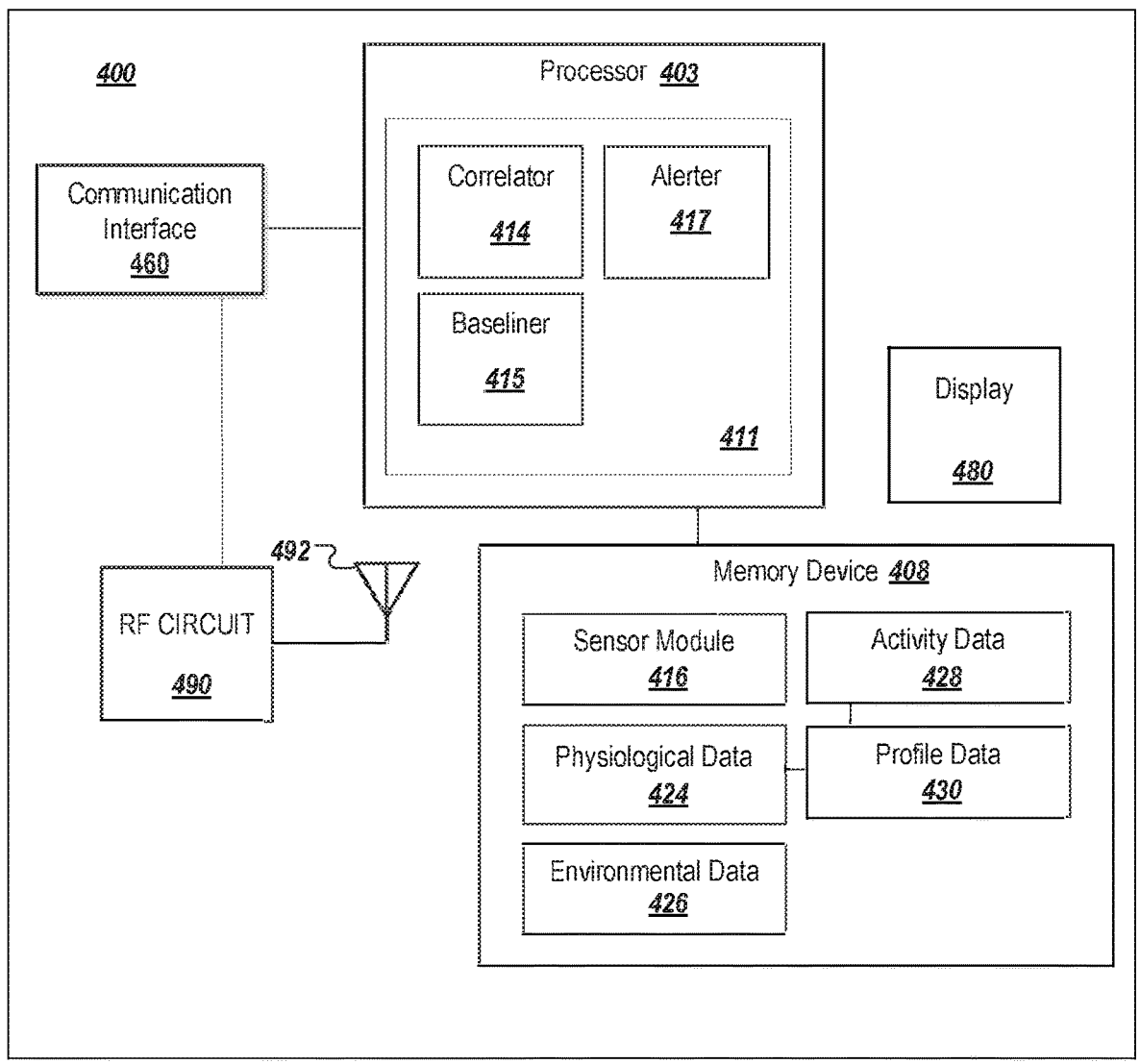
FIG. 4 is a block diagram of a networked device that communicates with UMD's according to one embodiment, and that includes the correlator and the baseliner.

FIG. 4 is a block diagram of a networked device 400 that communicates with UMD's according to various examples. In one embodiment, the network device 400 may be the hub (or base station) 120 illustrated in FIG. 1. In another embodiment, the network device 400 may be a server device such as the server 140 illustrated in FIG. 1. As such, the networked device 400 may include a communication interface 460 which with to communicate over the communications network 115. In some cases, the communication may be with the help of an RF circuit 490 and antenna 492, to communicate wirelessly, e.g., as may be used by the hub 120 (or a base station or a switch or the like that) at least in some implementations.

In these examples, the components of the networked device 400 are largely the same as those discussed above with reference to the UMD 110 of FIG. 3, with the exception of the sensors 302 and 304 and indicator(s) 318. Sensor data may be sent from the UMDs to the networked device over the network 115 and through the communications interface 460. Furthermore, any alerts or information for the user may be sent back to the UMD to initiate one of the indicator(s) 318 or provide information to the user through the display 380. The functions and capabilities of the UMD 110 of FIG. 3 may generally be replicated or enhanced by the functions and capabilities of the networked device 400 in terms of processing power, data analytics, performing correlations, predictions, analyzing and setting baselines, and other algorithmic work.

Accordingly, in one embodiment, the network device 400 may further include, without limitation, a processor 403, a memory device 408, and a display 480. The processor 403 may include a processing element 411 that may have a correlator 413, a baseliner 415 and an alerter 417. The memory device may include a sensor module 416, physiological data 424, environmental data 426, activity data 428 and profile data of and related to the users.

In one embodiment, the physiological sensors 302 and the activity sensors 304 of the UMD 110 may generate measurements, information and data that is stored in the memory device 308 of the UMD 110 as already discussed. In another embodiment, however, the UMD 110 may send this data and information to the networked device 400 to be stored as the physiological data 424, the environmental data 426, the activity data 428 and/or the profile data 430. The user profiles and, optionally, the baseline profiles of the users may also be stored with the profile data 430. And, as discussed previously, historical information may be stored by the networked device 400 that may help the networked device 400 with machine learning and to perform more intense processing and statistical analysis that may be required to implement the processes and strategies disclosed herein.

To do so, for example, the processing element 411 may function largely the same as the processing component 311 discussed with reference to the UMD 110 of FIG. 3, but with perhaps greater processing power and speed. In other words, the correlator 413 may function similarly to the correlator 313 upon receipt of the physiological, environmental and user data from the UMD 110 and/or from other sources. Those other sources may include cloud or internet servers that provide weather, altitude, geographic and location information, calendar and scheduling information, and other such information or data. Some of these sources may include other devices of the user such as a smartphone, tablet, a scale, a refractometer, a plasma osmolality device or other computing device that may or may not be tethered with the UMD 110, in alternative embodiments.

Furthermore, the baseliner 415 may function similarly to the baseliner 315 of the UMD 110 of FIG. 3 based on sensor data and other information received from the UMD 110 or the other sources. Additionally, the alerter 417 may function similarly to the alerter 317 of the UMD 110 of FIG. 3, based on sensor data and other information received from the UMD 110 or other sources.

In one embodiment, the UMD 110 may generate additional physiological and environmental data from on-going measurements. The user may also enter new information that may change the user's profile, such as a new age or position on a sport's team, and this information may also be sent by the UMD 110 to the networked device 400. When a baseline is set by the UMD 110 for a user as discussed previously, this baseline may also be sent to the networked device 400 where baselines for all users may be kept up to date, for purposes of tracking those users as well as providing data from which an initial baseline may be set for a physiological parameter of a newly added user. Furthermore, or alternatively, the baseline may be set by the baseliner 415 of the networked device 400 and sent to the UMD of the corresponding user against which new physiological measurements may be compared and/or correlated locally by the UMD.

Furthermore, any updates to a user profile, new physiological and/or environmental measurements may be sent to the networked device 400 by the UMD 110. As this type of information is updated, the networked device 400 may also update the baseline and/or baseline profiles of the users as disclosed herein. Any such updated baseline may be sent to the corresponding UMD 110 of the correct user, which UMD 110 may then update the baseline for that user locally.

Figure 5A:
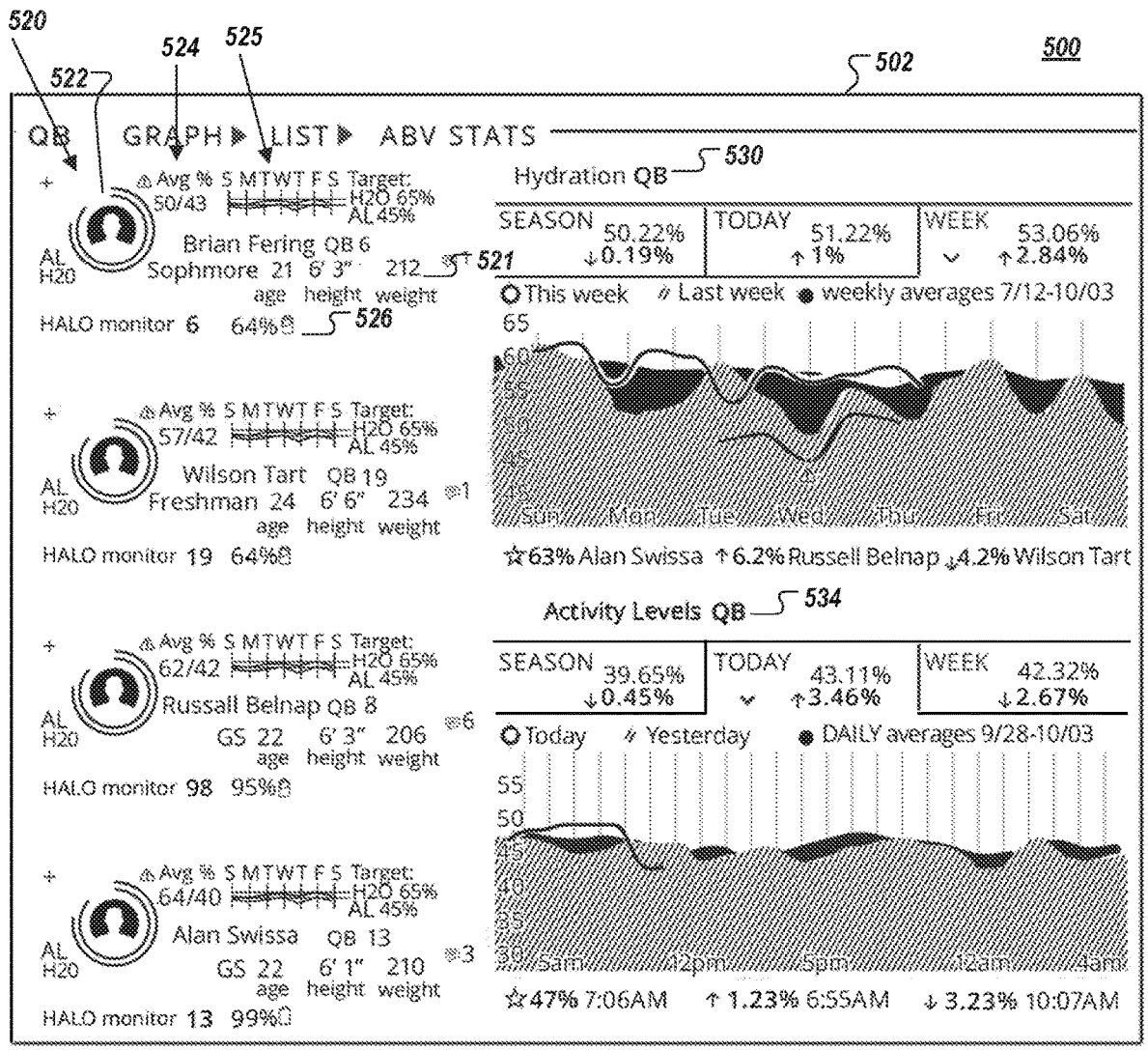
FIGS. 5A and 5B illustrate a group layer representation of a football team in a graphical user interface (GUI) according to one embodiment.
Figure 5A:
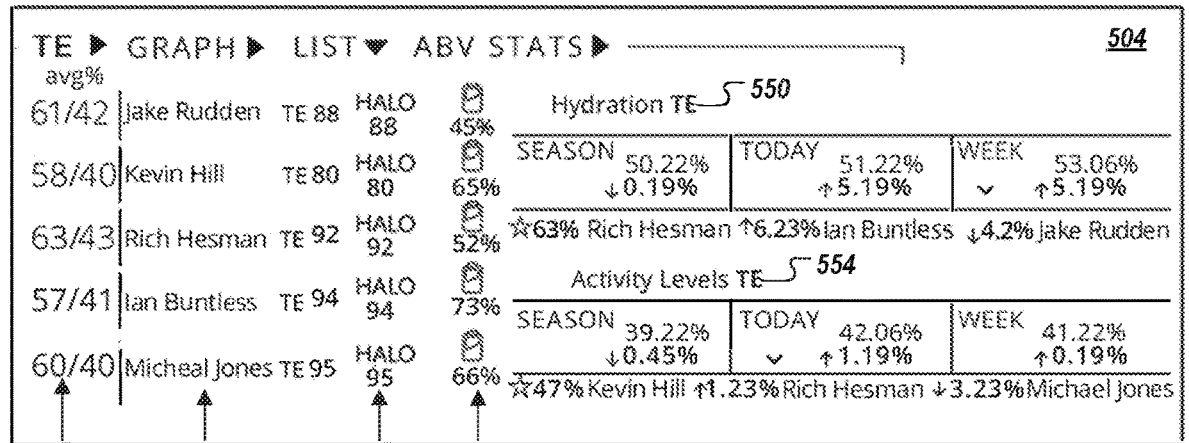
Figure 5B:
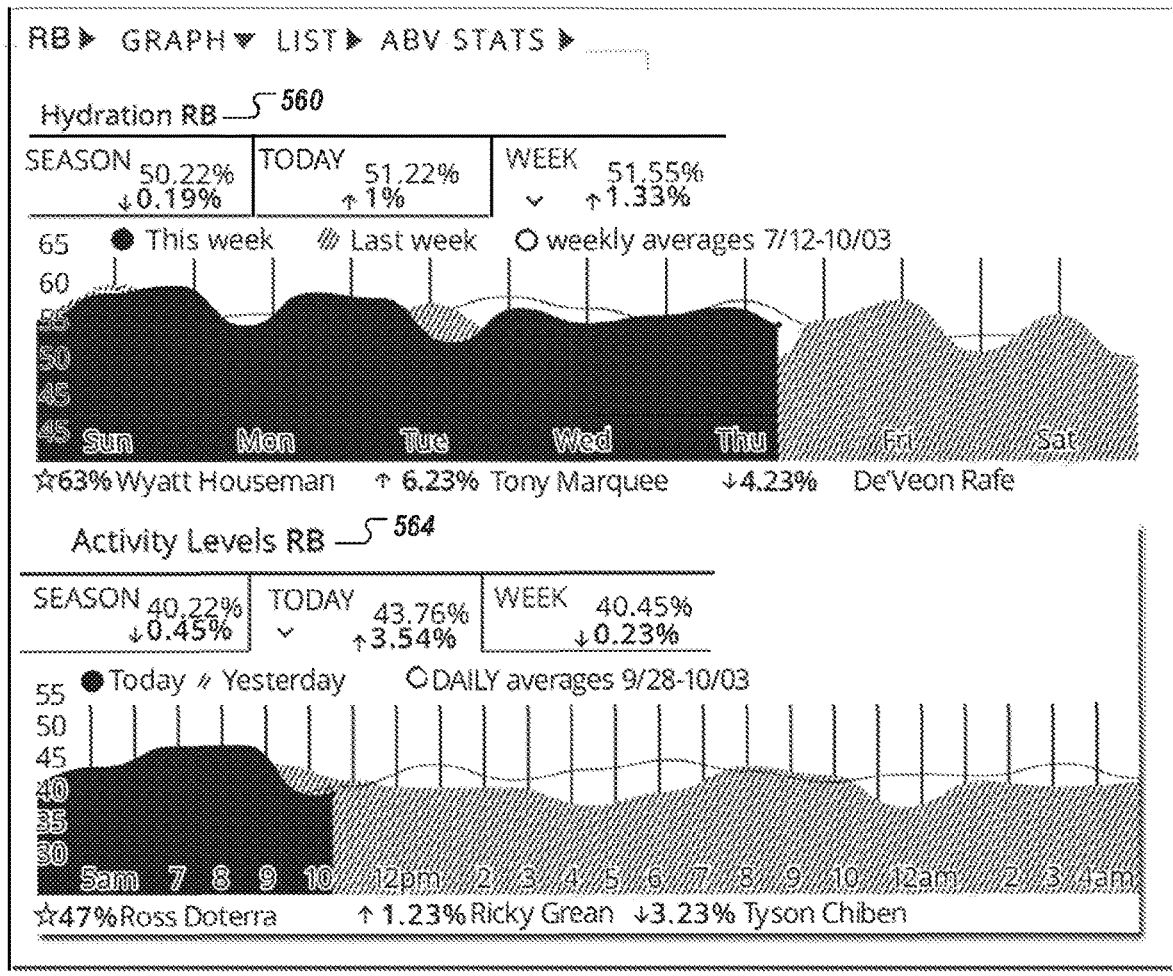
Figure 5B:
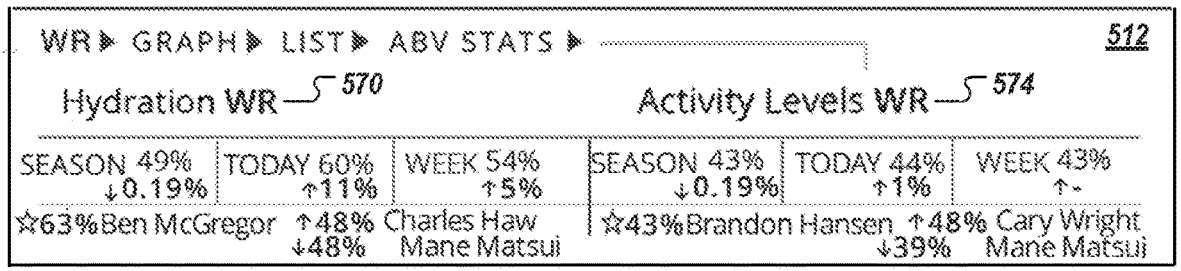
Figure 5B:
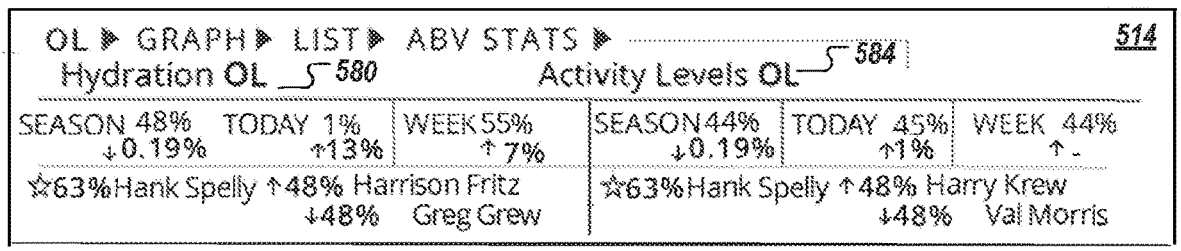

FIGS. 5A and 5B illustrate a group layer representation 500 of a football team in a graphical user interface (GUI) or other display according to one embodiment. Using the example of a football team, the group layer representation 500 may include, but not be limited to, a quarterback section 502, a tight end section 504, a running back section 508, a wide receiver section 512, and an offensive lineman section 514, each with varying amounts of profile information, physiological data, activity level data, and trending values of physiological parameter(s) and activity levels. This information may be provided through a GUI, touch screen or other display of any computing device including a smartphone, a tablet, a laptop, a desktop, or a server device, or any such device accessible by a coach, a trainer, medical specialists and/or the users of the UMDs disclosed herein. While hydration and activity levels are the two physiological parameters of focus in FIGS. 5A, 5B, 5C and 6, others are envisioned and therefore these are provided by way of example only.

In the present example, the quarterback section 502 may include user-specific data blocks 520, where for each user, the data block may include profile information 521, a physiological parameter status 522 (e.g., of activity level and hydration level), an average percentage 524 of hydration and activity level, respectively, a graph 525 of target hydration and activity level, and a battery level 526 for the UMD 110 of the user. The graph 525 may, in one embodiment, include curves for hydration and activity levels. A hydration target level and a target activity level may be shown at the right of, or otherwise in conjunction with, the graph 525.

In the user-specific data block 520, the users may be listed according to string (e.g., starting, first string, second string, etc.), alphabetically or based on other criteria. In FIG. 5A, Brian Fering is listed first followed by Wilson Tart and so forth through Alan Swissa. Each user's data block may be selectable to obtain more information for the specific user. For example, when the data block 520 (or portion thereof) for Brian Fering is selected, the screen of FIG. 5C may pop up to show additional details and statistics on Brian Fering (discussed below).

The quarterback section 502 may also include one or more trending blocks to show trending information for the quarterbacks as a whole. In the present example, the trending blocks may include a hydration trending block 530 and an activity level trending block 534, although others could be provided based on physiological parameters the coaches, trainer and/or users want to track. Each trending block may provide a season level (and how that compares with the previous season), today's level (and how that compares with the season level or a previous day level), and this week's level (and how that compares with the season level or a previous week). Each of the "season," "today," and the "week" may be selectable to be able to see trending data for, e.g., hydration and/or activity level, at different granularities. This information may be helpful to a coach, a trainer, team doctor or therapist and to the individual users to track progress over the season and during shorter periods of time, as well as to help set baselines for physiological parameters for new athletes to the team, as already discussed, or for previously injured or ill athletes that are returning to practice or higher levels of physical activity.

With continued reference to FIG. 5A, the tight end section 504 may include similar information to the quarterbacks, but in this case (and to save room), there may be less profile information. Accordingly, the tight end section 504 may include an average percentage 540 for hydration and activity level, respectively, over the season, each athlete's name 542, a UMD identifier 544, and a battery level 546 for the UMD of each respective tight end. The tight end section 504 may also include trending blocks including a hydration trending block 550 and an activity level trending block 554 with similar options as discussed with reference to the quarterback section 502. Each tight end in the tight end section 504 may be selectable (e.g., through a selection of the name of the tight end) to bring up more detail on the athlete such as shown in FIG. 5C.

With further reference to FIG. 5B, the running back section 508 may also include trending blocks for physiological (and other related) parameters such as activity level. In the present example, the trending blocks include a hydration trending block 560 and an activity level trending block 564 to shown similar information as discussed with reference to corresponding trending blocks in the quarterback section 502.

Other positions may include profile, physiological and other data as well, including, for example, in the wide receiver section 512 and the offensive lineman section 514. In FIG. 5B, the wide receiver section 512 may include a hydration trending block 570 and an activity level trending block 574, with selectable sections to provide granularity to inspect the season, today, or this week's trending data. The offensive lineman section 514 may also include a hydration trending block 580 and an activity level trending block 584, with selectable sections to provide granularity to inspect the season, today, or this week's trending data. This information may be helpful to a coach, a trainer, medical personnel and/or to the individual users to track progress over the season and during shorter periods of time, as well as to help set baselines for physiological parameters for new or returning athletes to the team, as already discussed.

Figure 5C:
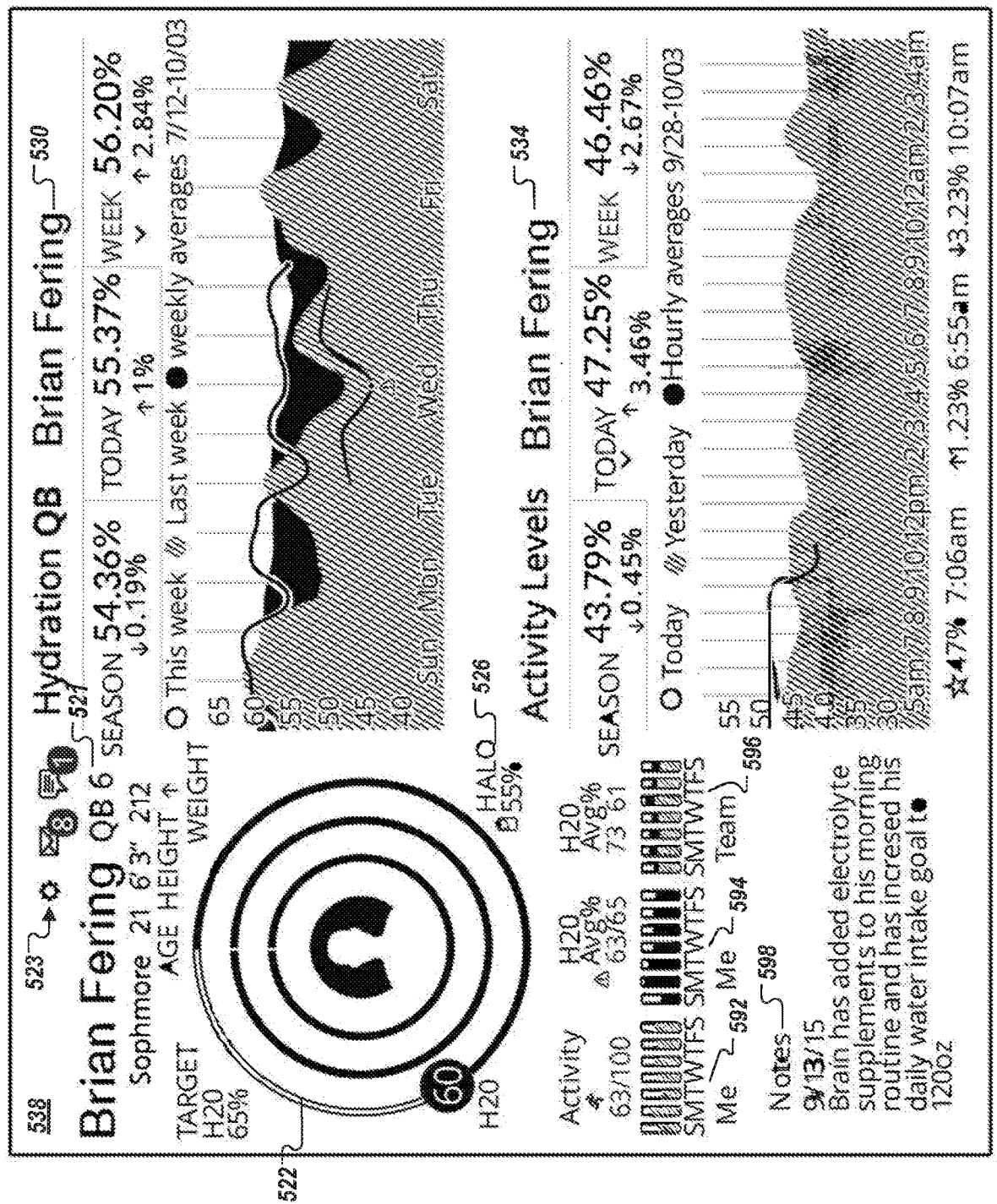
FIG. 5C illustrates a detailed individual layer representation of one of the quarterbacks in the GUI according to one embodiment.

FIG. 5C illustrates a detailed individual layer representation 538 of one of the quarterbacks in the quarterback section 502 of FIG. 5A, according to one embodiment. This individual layer representation 538 may result from the selection of "Brian Fering" in the user specific data block 520 for Brian Fering (e.g., selection of Brian Fering's name or other profile information for Brian Fering), and in one embodiment, may be a pop-up window that is displayed in the GUI. The detailed individual layer representation 538 may include an information settings block 523, to include settings, email, and messages, the latter of which may facilitate the user (Brian Fering) communicating regarding his training regime, for example, with a coach, trainer and/or medical person.

The detailed individual layer representation 538 may include much of the same information as displayed in the quarterback section 502 in the group layer representation 500 in FIG. 5A, but with some of the information and data customized to the selected athlete, e.g., Brian Fering. For example, the physiological parameter status 522 may include current levels of physiological parameters, including hydration (shown as "60" currently for Brian Fering), heart rate, core or skin temperature, blood pressure, tissue bulk absorption, bio-impedance spectroscopy and the like. Furthermore, the hydration trending block 530 may be customized to Brian Fering's hydration data, and therefore exclude the rest of the quarterback's hydration data. Similarly, the activity level trending block 534 may be customized to Brian Fering's activity levels, and therefore exclude the rest of the quarterback's activity level data.

The graphs on the right in FIGS. 5A and 5C and the graphs of FIG. 5B show a layering of the different measurement information which can indicate a correlation between the different measurements. Additional trending graphs may be provided to help compare the selected user's physiological data to that of the team's. For example, the individual layer representation 538 may also include a weekly activity trending graph 592 and a weekly hydration trending graph 594 (compared to target values) and a comparative team trending graph 596 for both hydration and activity level. The individual layer representation 538 may further include a notes section 598 for brief notes about nutrition regimes, workout schedules and adjustments, and medical conditions or reactions to team or individual training.

Figure 6:
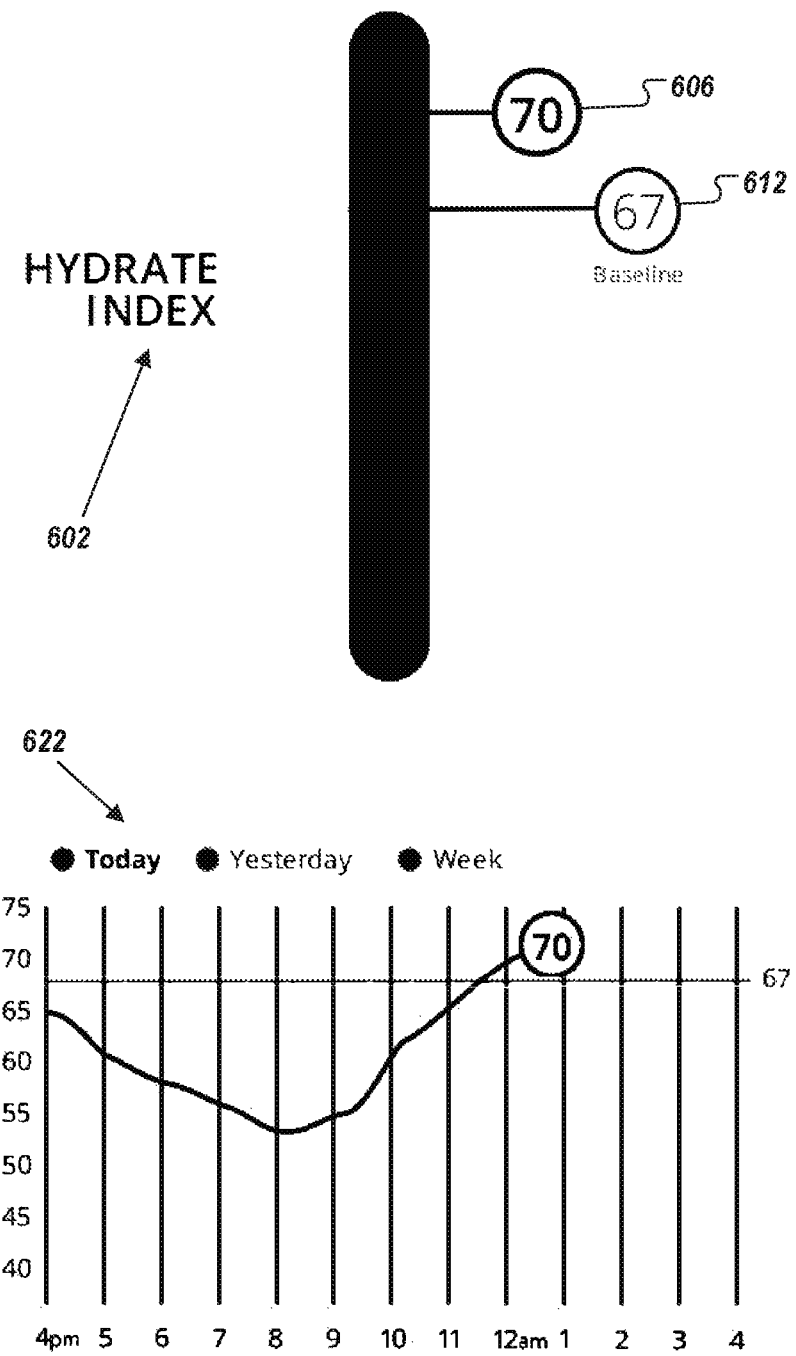
FIG. 6 illustrates a hydration index comparing a user's current hydration to a baseline of hydration for the user.

FIG. 6 illustrates a screenshot 600 of a hydration index 602 comparing a user's current hydration 606 to a baseline 612 of hydration for the user. A chart or table 622 may all visualizing the user's hydration 606 benchmarked against the baseline 612 for the user. The chart 622, in various embodiments, may be adapted to show different granularities, e.g., to include trending data over several days, a week or more.

Figure 7A:
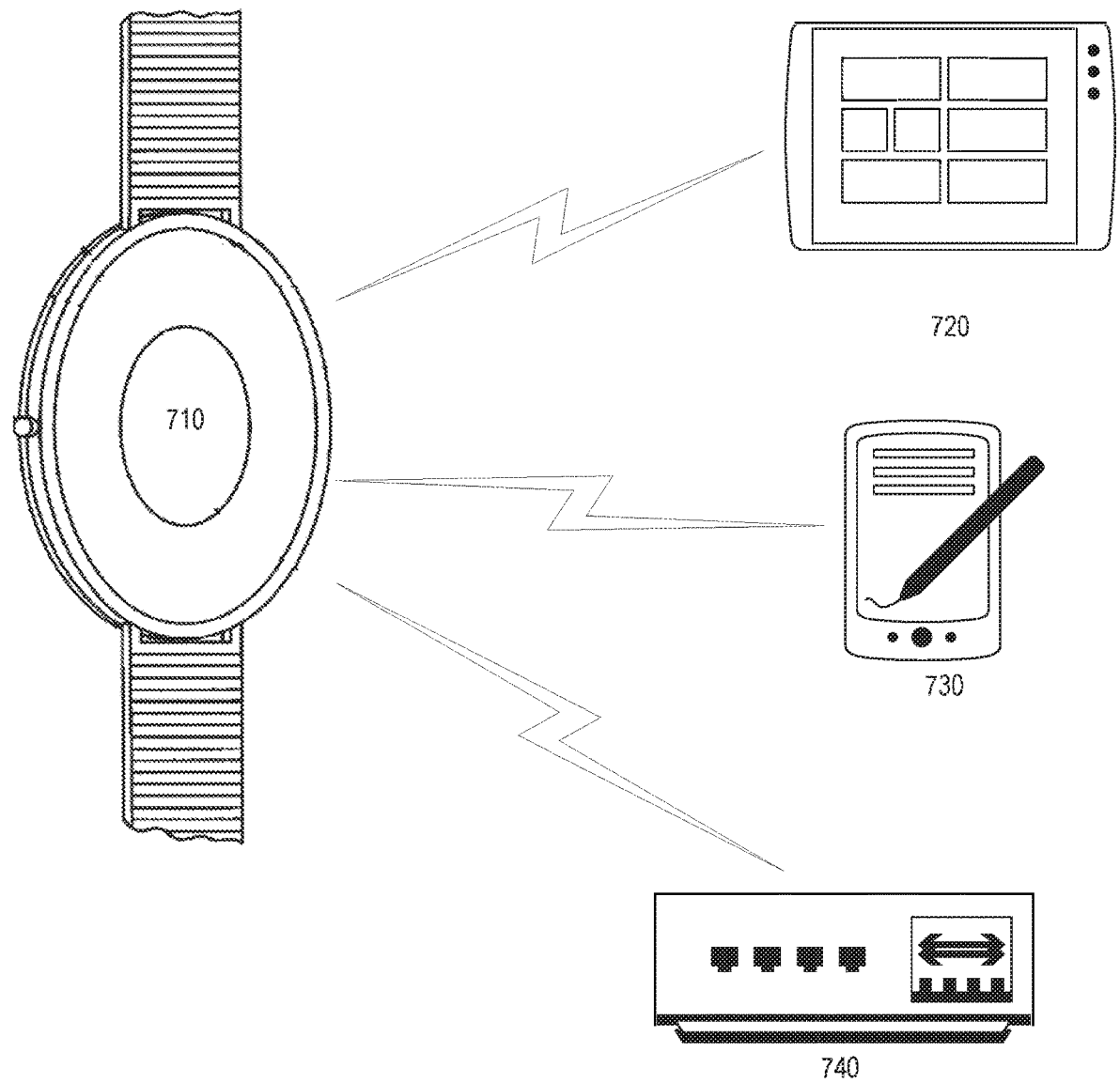
FIG. 7A depicts a base station or a UMD configured to communicate data with one or more other devices according to one embodiment.

FIG. 7A depicts a base station and/or a UMD 710 configured to communicate data, such as input data, with one or more other devices such as a tablet computer 720, a smartphone 730, and/or other computing device 750 according to one embodiment. In various other embodiments, the other devices may be non-wearable and/or non-portable devices, such as a bathroom scale or a bed scale 720, a medical device 730, and/or a continuous positive airway pressure (CPAP) device 750. In another embodiment, the base station and/or the UMD may store and/or analyze the data received from the one or more other devices separately from data of the base station and/or the UMD. In another embodiment, the base station and/or the UMD may aggregate the data received from the one or more other devices with the input data of the base station and/or the UMD. In another embodiment, the base station and/or the UMD may store, synchronize, and/or analyze the aggregated data of the one or more other devices and the base station and/or the UMD.

Figure 7B:
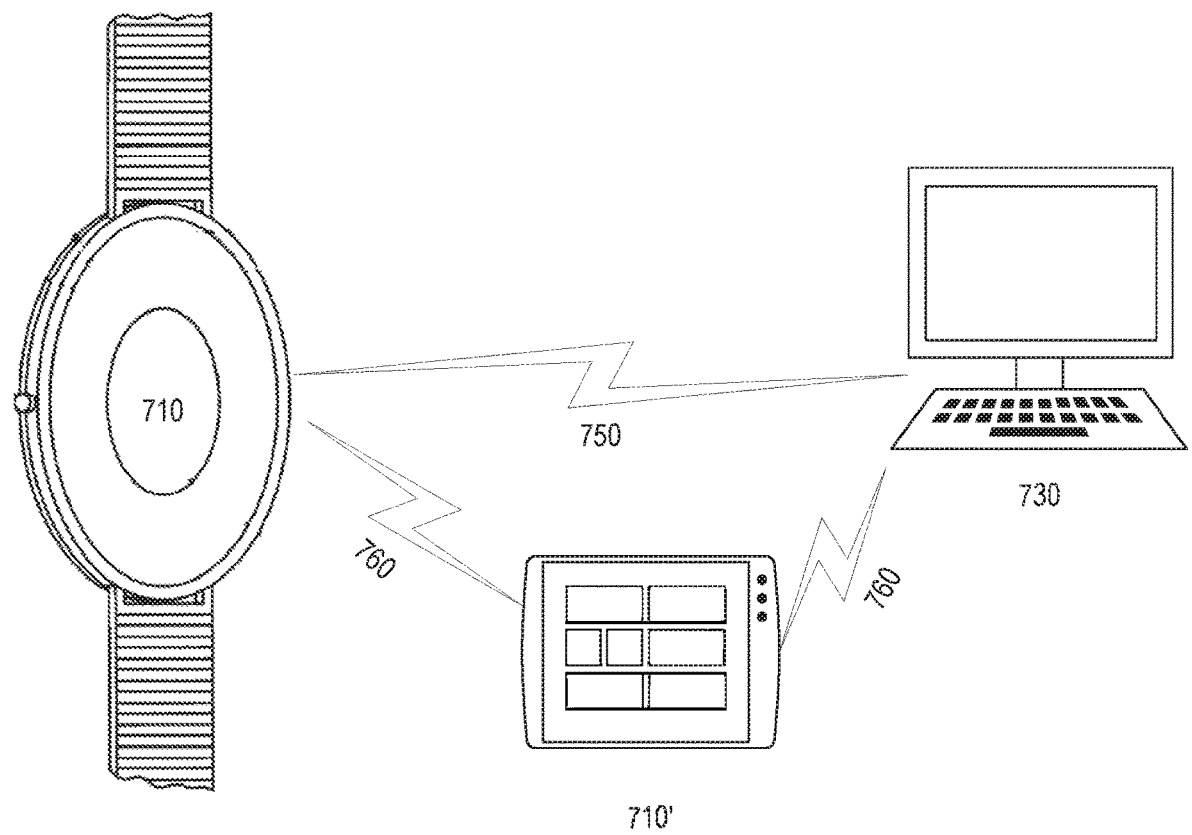
FIG. 7B illustrates a base station or a UMD operable to communicate sync data to a computing device according to one embodiment.

FIG. 7B illustrates a base station and/or a UMD 710 operable to communicate input data to a computing device 730, such as the hub 120 or server 150 according to two embodiments. In one example, the base station and/or the UMD 710 may communicate input data directly to the computing device 730 using a communications connection 750 of a communications network. In another example, the base station and/or the UMD 710 may indirectly communicate the input data to the computing device 730 using another base station or another UMD 710 along communication connections 760.

FIG. 7B further illustrates that the base station and/or a UMD 710 may receive selected data or information, such as input data or other information, from the computing device 730. In one example, the base station and/or a UMD 710 may receive selected data or information for a user of the base station and/or a UMD 710 from a cloud-based server or a server in communication with a cloud-based server.

In one embodiment, the input data may include setting information for the base station and/or a UMD 710. In one example, the setting information may include measurement data threshold ranges, measurement data threshold values, measurement event triggering values, and so forth. In another example, the input information may include medical information of the user of a UMD, user condition information, medication regiment information, exercise regimen information, medical risk information, and so forth.

In another embodiment, the UMD 710 and/or the base station may provide a sensory indication (such as a visual, auditory, and/or touch indication) communicating the selected data or information to the user. In one example, the UMD and/or the base station 710 may display a reminder for a user to exercise, take medication, rehydrate, and so forth.

In one embodiment, the base station may analyze received input data and/or stored input data (such as measurement information) to determine selected states or conditions, such as medical conditions, physiological states, and so forth of the user of the UMD. In another embodiment, the base station may aggregate input data received from a plurality of UMDs. In another embodiment, the base station may aggregate current input data received from one or more UMD or other base stations with previous input data stored at the base station or a device in communication with the base station. In another embodiment, the base station may analyze the aggregated sync data.

In one configuration, the base station may communicate other information to one or more UMDs. For example, the base station may receive software and/or firmware update information and relay the software and/or firmware update to the one or more UMDs. In one embodiment, the base station may communicate the other information to the one or more UMDs when the one or more UMDs receive energy (such as wired energy or wireless energy) from the base station.

Figure 8:
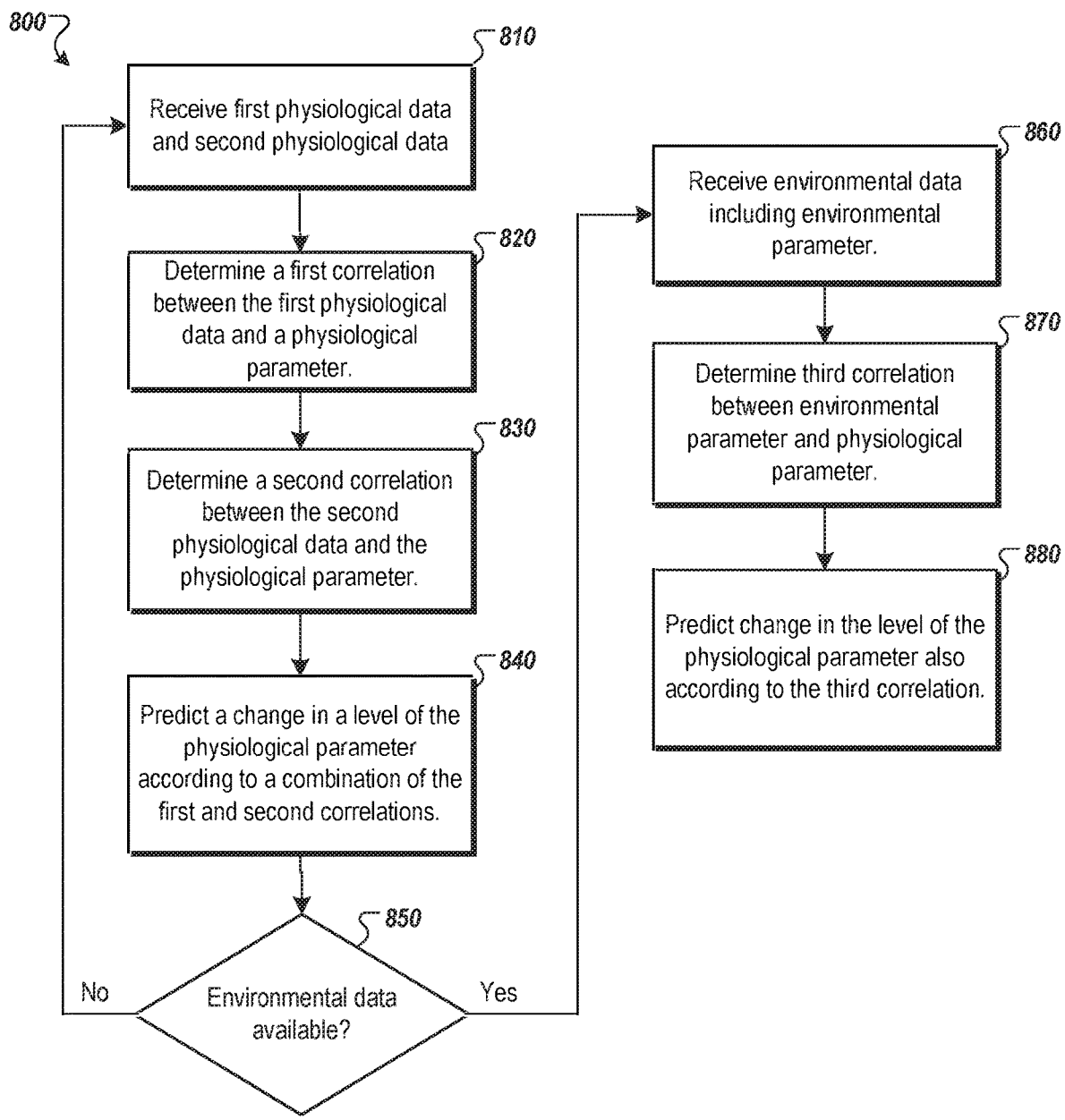
FIG. 8 is a flow chart of an exemplary method for correlating physiological data to predict a change in a physiological parameter according to one embodiment.

FIG. 8 is a flow chart 800 of an exemplary method for correlating physiological data to predict a change in a physiological parameter. In one embodiment, the method includes receiving the first physiological data and the second physiological data (810). The method may further include analyzing the first physiological data to determine a first correlation between the first physiological data and a physiological parameter (820) and analyzing the second physiological data to determine a second correlation between the second physiological data and the physiological parameter (830). The method may also include predicting a change in a level of the physiological parameter according to a combination of the first correlation and the second correlation (840). In just one example, the first physiological data includes optical spectroscopy (or luminosity) levels, the second physiological data skin impedance levels, and the physiological parameter includes hydration or activity level.

The first and second physiological data may be obtained from other than the physiological parameter. For example, if the physiological parameter to be predicted is hydration, the physiological data from which the correlation is made will not be direct hydration measurements, but could be, for example, measurements such as bioimpedance spectroscopy or optical spectroscopy data that may relate to hydration. As another example, if the physiological parameter to be predicted is electrolyte levels of an athlete, then the first and second physiological data may come from other than direct electrolyte level measurements.

The embodiment of the method of FIG. 8 may further decide whether environmental data is also available related to the physiological parameter (850). If not, the method may loop back to block 810. If yes, the method may receive environmental data including an environmental parameter (860). The method may further include analyzing the environmental data to determine a third correlation between the environmental parameter and the physiological parameter (870). The method may then include predicting the change in the level of the physiological parameter also according to the third correlation (880).

In one embodiment, the first physiological data and the second physiological data may be taken during a first time period, and the change in the level of the physiological parameter is predicted for a second period such as immediately following the first time period, corresponding to the first time period on a subsequent day or during a future day while the user performs a similar or identical activity. In this way, the method may include analyzing the physiological data of previous time periods or during a current time period at which time a correlation is made.

Figure 9:
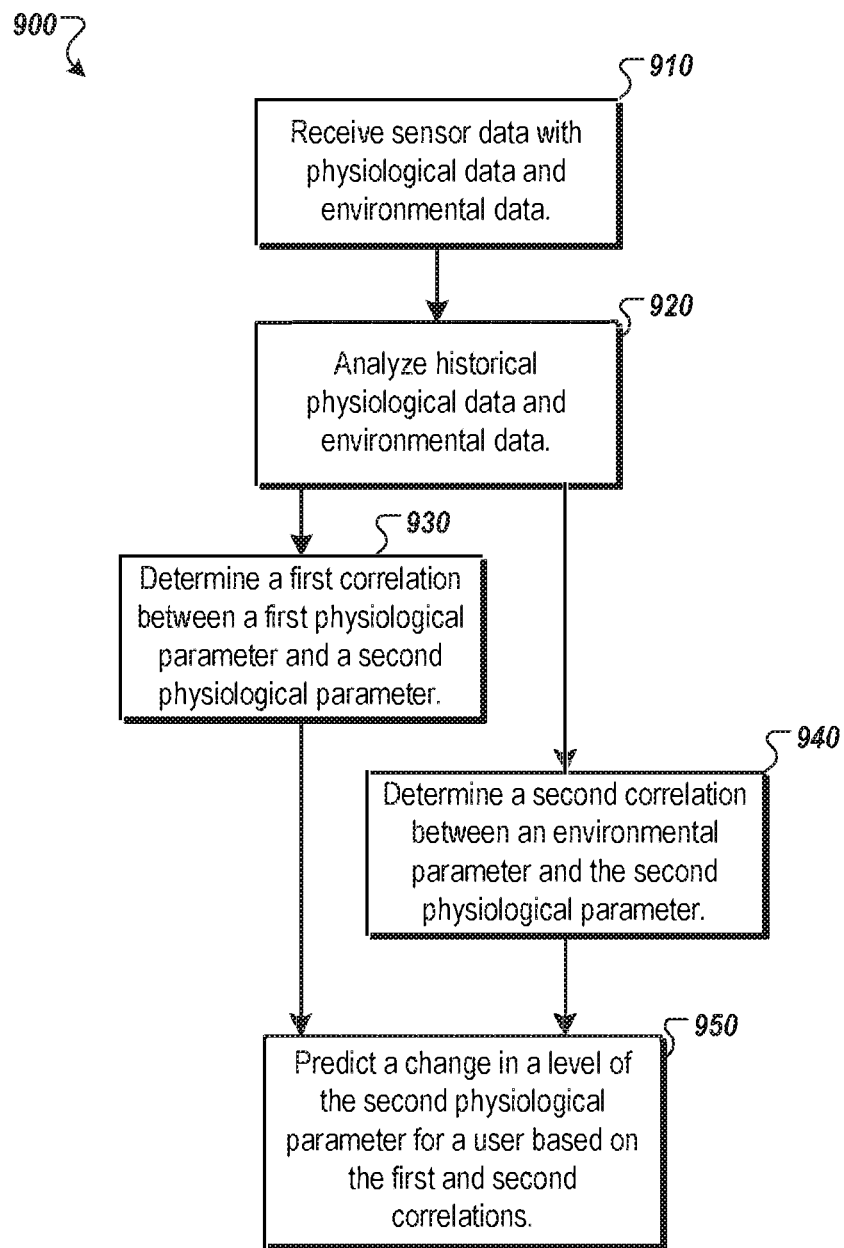
FIG. 9 is a flow chart of an exemplary method for analyzing historical physiological data and environmental data to predict a change in a physiological parameter according to one embodiment.

FIG. 9 is a flow chart 900 of an exemplary method for analyzing historical physiological data and environmental data to predict a change in a physiological parameter. The method may include receiving sensor data comprising physiological data and environmental data (910). The method may then include analyzing historical physiological data and environmental data (920) to determine a first correlation between a first physiological parameter and a second physiological parameter (930) and a second correlation between an environmental parameter and the second physiological parameter (940). The method may also include predicting a change in a level of the second physiological parameter of an identified person for which the physiological data is received based on the first correlation and the second correlation (950).

In one example, the second physiological parameter is hydration or oxygenation. The first physiological parameter may be something other than the second physiological parameter, including, heart rate, skin temperature, tissue bulk absorption, bio-impedance spectroscopy, or blood pressure. In one embodiment, the environmental data may be temperature, ambient humidity, altitude, geographical location, and/or time of day. The historical physiological data may be of the identified person or of a group of persons.

In some embodiments, the method may also determine that the first correlation is below a threshold correlation for the first physiological parameter and disregard the first correlation when predicting the change in the level of the second physiological parameter. Additionally, or alternatively, the method may determine that the second correlation is below a threshold correlation for the environmental parameter and disregard the second correlation when predicting the change in the level of the second physiological parameter.

Figure 10:
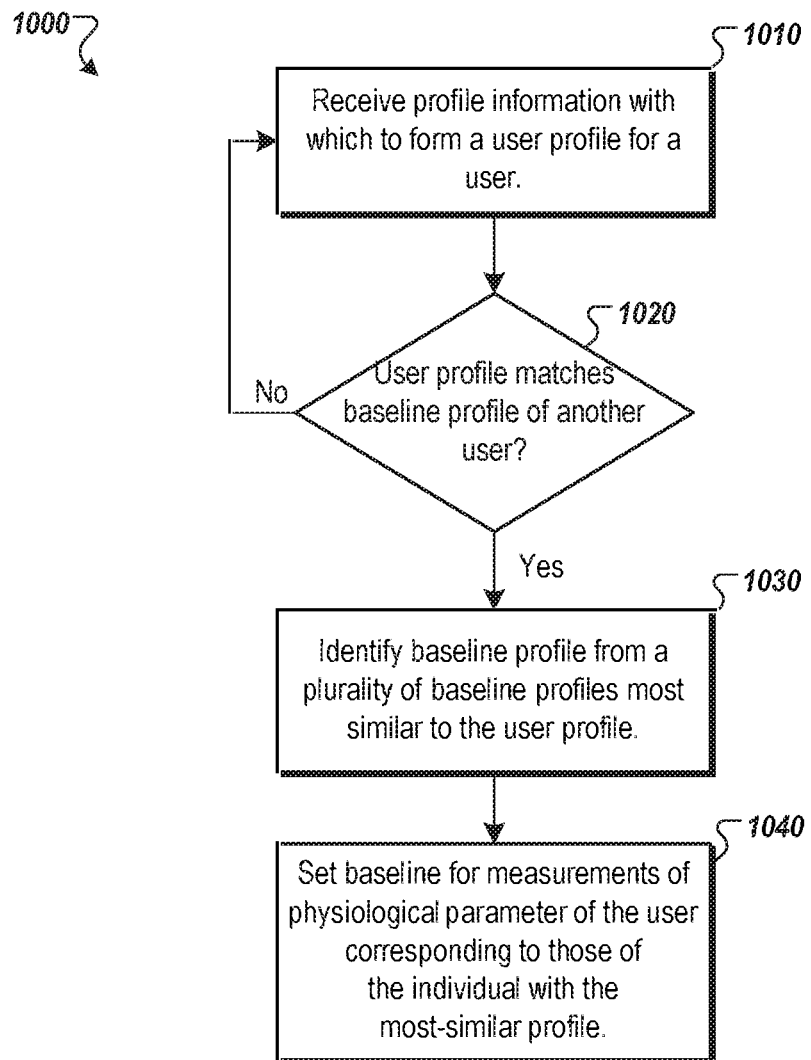
FIG. 10 is a flow chart of an exemplary method for setting a baseline for a physiological parameter based on a most-similar baseline profile of another according to one embodiment.

FIG. 10 is a flow chart 1000 of an exemplary method for setting a baseline for a physiological parameter based on a most-similar baseline profile of another. The method may include receiving and storing in a memory device as a user profile (1010). The profile information for a user may include gender, age, weight, health, and fitness level, as well as family health histories. The method may further include detecting profile matches with baseline profiles of other users (1020). When there are none, the method may loop back to block 1010. When there are matches, the method may further include identifying the baseline profile, from all of the matching baseline profiles of the users, the one that is most similar to the user profile based on a correlation between the user profile information and baseline profile information (1030). The method may then set a baseline for measurements of a physiological parameter of the user corresponding to levels of the physiological parameter of an individual with the baseline profile that is most-similar (1040). The user may then, based on measurements of the physiological parameter, be informed (e.g., through a display, indicator or graphical user interface) whether the measurements are above or below the baseline and by how much. In one example, those measurements may be averaged over a period of time (such as an hour, a workout, or over a period of day(s)) before being compared with the baseline.

In additional embodiments, the baseline may later be updated based on updated profile information, including trending changes in the physiological parameter of the user, and/or on correlations between research information and measurements of the physiological parameter.

In one embodiment, to identify the baseline profile, the method may include applying weights to a plurality of traits within the user profile, to generate a plurality of weighted traits, and matching the weighted traits with corresponding levels of the weighted traits within the plurality of baseline profiles. Furthermore, in at least one embodiment, the method may set the baseline for the physiological parameter as an average of the levels of the physiological parameter of a determined number of individuals with most-similar profiles.

In applying weighting as disclosed herein, the processor 303 or 403 may be adapted to dynamically weight certain data for a user, taking into consideration that a fitness level of the user may change over time, a metabolic rate of the user may change over time, a sweat rate of the user may change over time, such as staying more hydrated with the same amount of fluids, an average heart rate of the user may change over time, and the like. In one embodiment, these types of measurements may be weighted temporally, where more recent measurements are weighted more highly than older measurements.

Alternatively, or additionally, these types of measurements may be weighted according to the consistency of data based on an analysis of a statistical distribution of the measurements. For example, measurement data that has little statistical variation may be weighted higher than data with a scattered statistical distribution.

Alternatively, or additionally, these types of measurements can be weighted according to the outcome as measured against a known standard. For example, heart rate for a user can be measured against a target heart rate for users of the same age, and data from other users of the same age group may be weighted higher for a comparison base. This sort of outcome weighting may be performed as a multivariate analysis of a number of parameters weighted according to the importance of outcome or comparison with a known standard.

Alternatively, or additionally, these types of measurements may be weighted based on the quality of the data, as discussed in the preceding paragraphs. For example, data with a higher signal-to-noise (SNR) or from a preferred, more reliable, source may be weighted higher than data with a lower SNR or from a questionable source.

The present weighting methods, as described herein, may then be blended to weave in different sources and types of data into a multifactor analysis in which one or more of the above weighting schemes can be employed. In one embodiment, these weightings are performed as coefficients of multiple polynomials in an algorithm, formula or statement that forms a part of an analysis regarding a user, generates a user profile, a diagnosis or a performance-based recommendation provided to a user, as just a few non-exhaustive examples.

Figure 11:
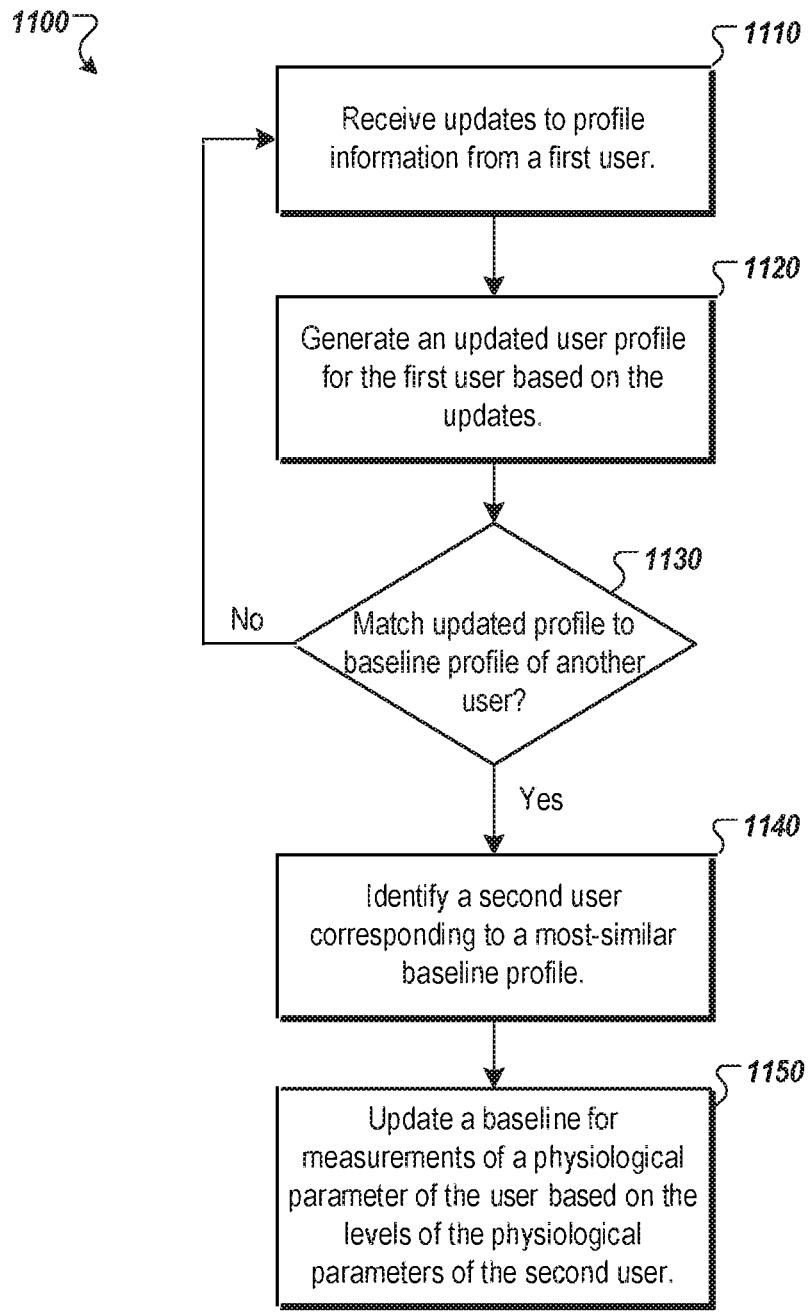
FIG. 11 is a flow chart of an exemplary method for updating a baseline for a physiological parameter based on an update to profile information of a user according to one embodiment.

FIG. 11 is a flow chart 1100 of an exemplary method for updating a baseline for a physiological parameter based on an update to profile information of a user. The method may include receiving updates to profile information from a first user (1110). Such profile information may include gender, age, weight, health, and fitness level, as well as family health history and the like. The method may further include generating an updated user profile for the first user based on the updates (1120). The method may then detect profile matches of the updated user profile with baseline profiles of other users that are most similar to the user's updated profile (1130). When there are no matches sufficiently close (e.g., a threshold matching level) to the user's updated profile, the method may loop back to block 1110. When there are matches, the method may include identifying a second user corresponding to a most-similar baseline profile to that of the updated user profile (1140). The method may then update a baseline for measurements of a physiological parameter of the user based on levels of the physiological parameter of the second user, to generate an updated baseline for the user (1150). The user may then, based on measurements of the physiological parameter, be informed (e.g., through a display, indicator or graphical user interface) whether those measurements are above or below the updated baseline and by how much. In some example, the measurements are averaged over a period of time.

In an alternative embodiment, the second user may be a group of users, and/or the levels of the physiological parameter of the group of users may be an average of the levels across individuals of the group of users. In such a case, the baseline may be set instead with respect to the group of users.

Figure 12:
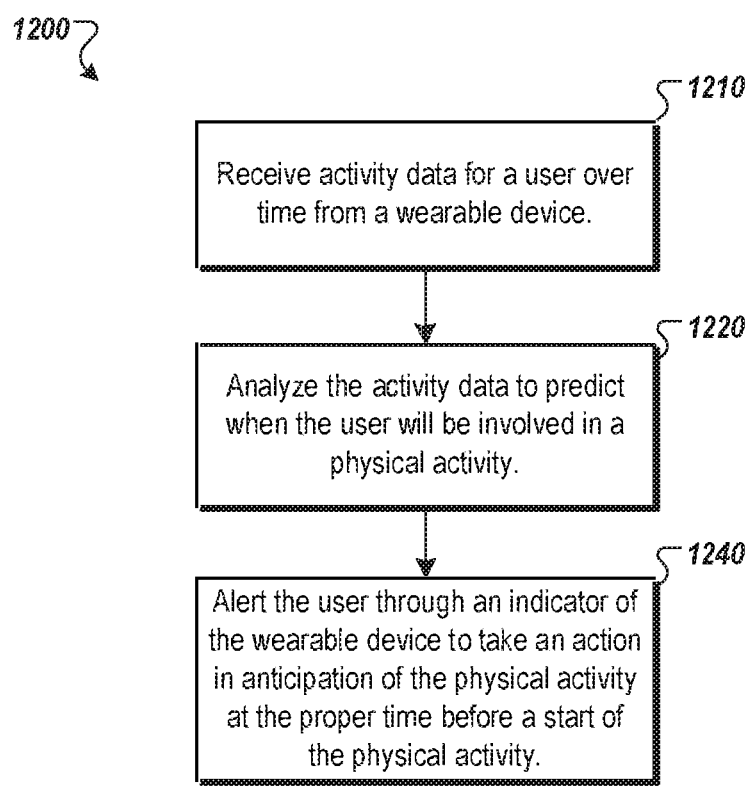
FIG. 12 is a flow chart of an exemplary method for alerting a user through an indicator of a wearable UMD in anticipation of undertaking a physical activity according to one embodiment.

FIG. 12 is a flow chart 1200 of an exemplary method for alerting a user through an indicator of a wearable UMD in anticipation of undertaking a physical activity. The method may include receiving activity data for a user over time (1210). The method may further include analyzing the activity data to predict when the user will be involved in a physical activity (1220). The method may further include alerting the user through the indicator to take an action in anticipation of the physical activity at a proper time before a start of the physical activity (1240). In one embodiment, the alert may be sent over a network between a networked device and the UMD. The specific action may be actions such as to hydrate, to eat, to rest or to warm up. The proper time may be determined by how far before the physical activity the user may need to perform the specific action (e.g., hydrating continuously starting 4 to 8 hours before, eating at least 2 hours before, and warming up starting 20-30 minutes prior to the physical activity), and which may be customized by a trainer, coach, medical person or the user.

In some embodiments, the method includes machine learning habits of the user involving differing activity levels of the user based on the analyzed activity data over time. Through machine learning of these habits, the method may be able to predict what kind of activity the user undertakes depending on the day and time of day, and even in some cases, the period of time during the year.

The method may further include selecting from a plurality of indicators depending on a type of the physical activity or the nature of the specific action to be taken, e.g., selected from two or more of a light, a display, a speaker, a vibrator, and a touch screen.

In one embodiment, the activity data may include activity levels related to geographic locations of the user, and the method may further include determining a correlation between information from the activity data and the physical activity and identifying the physical activity as a probable activity the user will undertake based on the correlation.

In another embodiment, the activity data may include scheduling data including upcoming appointments of the user, where the method may further include identifying additional information that indicates an appointment corresponding to the physical activity relates to a nonphysical activity and adjusting the alert (sent in block 1240) to the user to account for a likelihood that the appointment relates to a nonphysical activity.

In a further Example 1, a computing device may include 1) a memory device for computer storage; 2) a display having a user interface for engagement by a user; and 3) a processing device to: a) store, in the memory device, input data including environmental data and physiological data, the physiological data received from a sensor in bodily engagement with the user; b) analyze the input data to identify a trend in one or more physiological parameters of the user; and c) display the input data in the user interface to alert the user of the trend.

In an Example 2, the computing device Example 1 may further include a housing formed and shaped to affix to a user, wherein the sensor is integrated into the housing such as to make contact with a body of the user.

In an Example 3, the computing device of claim Example may further include a communication interface to send the input data to a networked device over a network, for storage in the networked device.

In an Example 4, the computing device of Example 1, wherein the input data further includes an activity level of the user and the trend comprises a first trend, wherein the processing device is further to: a) analyze the input data to identify a second trend in the activity level; b) analyze the input data to identify a third trend in an environmental parameter; and c) display the input data in the user interface to alert the user of the second trend or of the third trend.

In an Example 5, the computing device of Example 1, wherein the environmental data and physiological data includes, respectively, first environmental data and first physiological data related to the user, and wherein the input data further includes second environmental data and second physiological data stored for a group of users.

In an Example 6, the computing device of Example 5, wherein the processing device is further to sort a plurality of environmental parameters and physiological parameters from the first and second physiological data and from the first and second environmental data, the plurality of environmental parameters and physiological parameters comprising any or a combination of: a time of day, a day of week, group information, individual user information, a measurement type, a measurement duration, an activity type, a piece of profile information, injury information, and performance information.

In an Example 7, the computing device of Example 5, wherein the input data further includes user-specific profile information for the group of users, and the processing device is further to: a) index the input data for the group of users at a group level to generate a group database; b) index individual user input data on an individual level to generate a plurality of individual databases; and c) make the group database and the plurality of individual databases searchable through the user interface.

Figure 13:
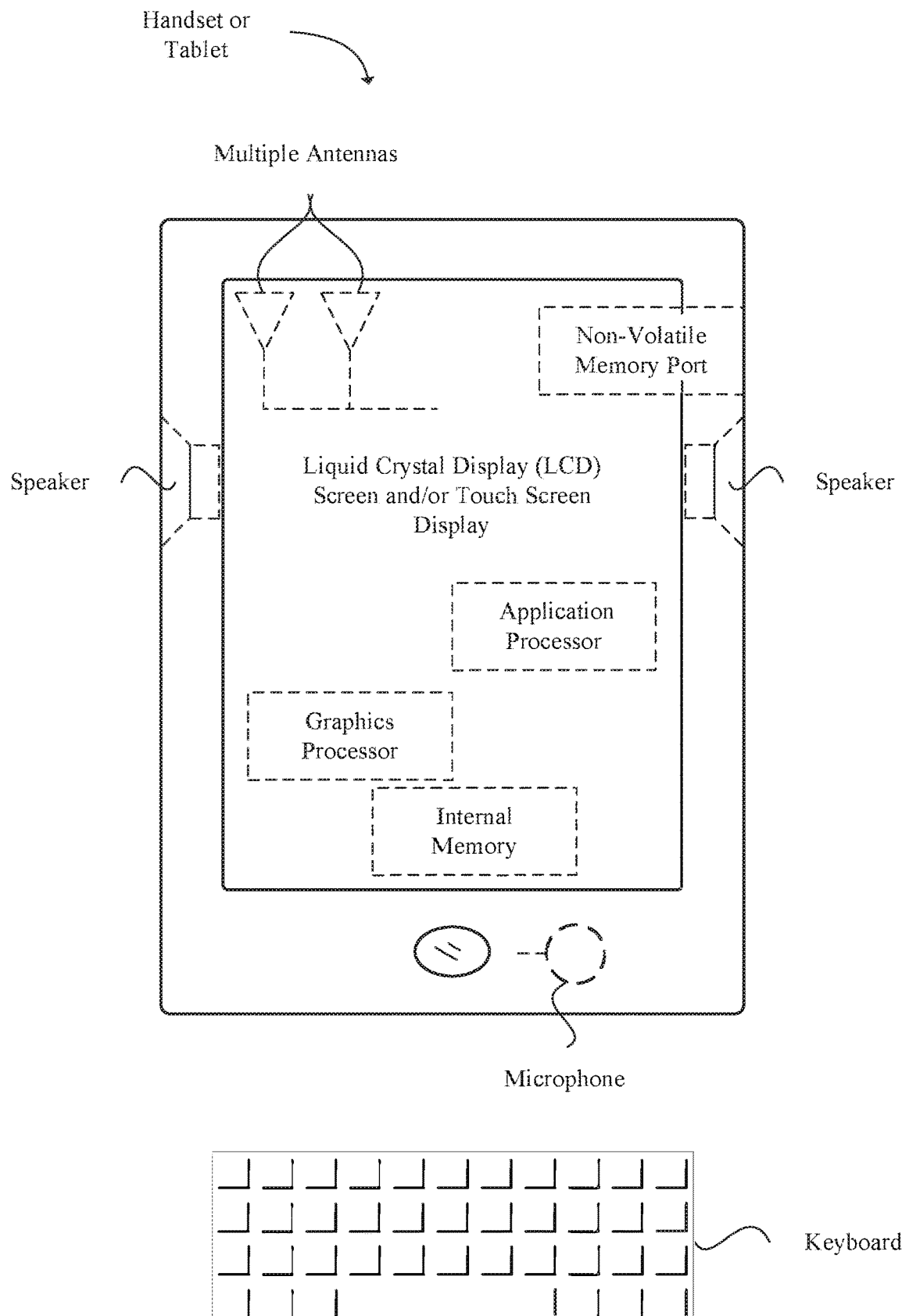
FIG. 13 illustrates a diagrammatic representation of a machine in the example form of a computer system within which a set of instructions, for causing the machine to perform any one or more of the methodologies discussed herein, may be executed.

FIG. 13 provides an example illustration of a processing device disclosed herein, such as a user equipment (UE), a base station, a UMD, a mobile wireless device, a mobile communication device, a tablet, a handset, or other type of wireless device according to one embodiment. The device may include one or more antennas configured to communicate with a node or transmission station, such as a base station (BS), an evolved Node B (eN ode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device may be configured to communicate using at least one wireless communication standard including 3GPP LTE, WiMAX, High-Speed Packet Access (HSPA), Bluetooth, and Wi-Fi. The device may communicate using separate antennas for each wireless communication standard or shared antennas for multiple wireless communication standards. The device may communicate in a wireless local area network (WLAN), a wireless personal area network (WPAN), and/or a WWAN.

FIG. 13 also provides an illustration of a microphone and one or more speakers that may be used for audio input and output from the device. The display screen may be a liquid crystal display (LCD) screen, or other type of display screen such as an organic light emitting diode (OLED) display. The display screen may be configured as a touch screen. The touch screen may use capacitive, resistive, or another type of touch screen technology. An application processor and a graphics processor may be coupled to internal memory to provide processing and display capabilities. A non-volatile memory port may also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the invention. One skilled in the relevant art will recognize, however, that the invention may be practiced without one or more of the specific details, or with other methods, components, layouts, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage, and details of implementation may be made without the exercise of inventive faculty, and without departing from the principles and concepts of the invention. Accordingly, it is not intended that the invention be limited, except as by the claims set forth below.

Figure 14:
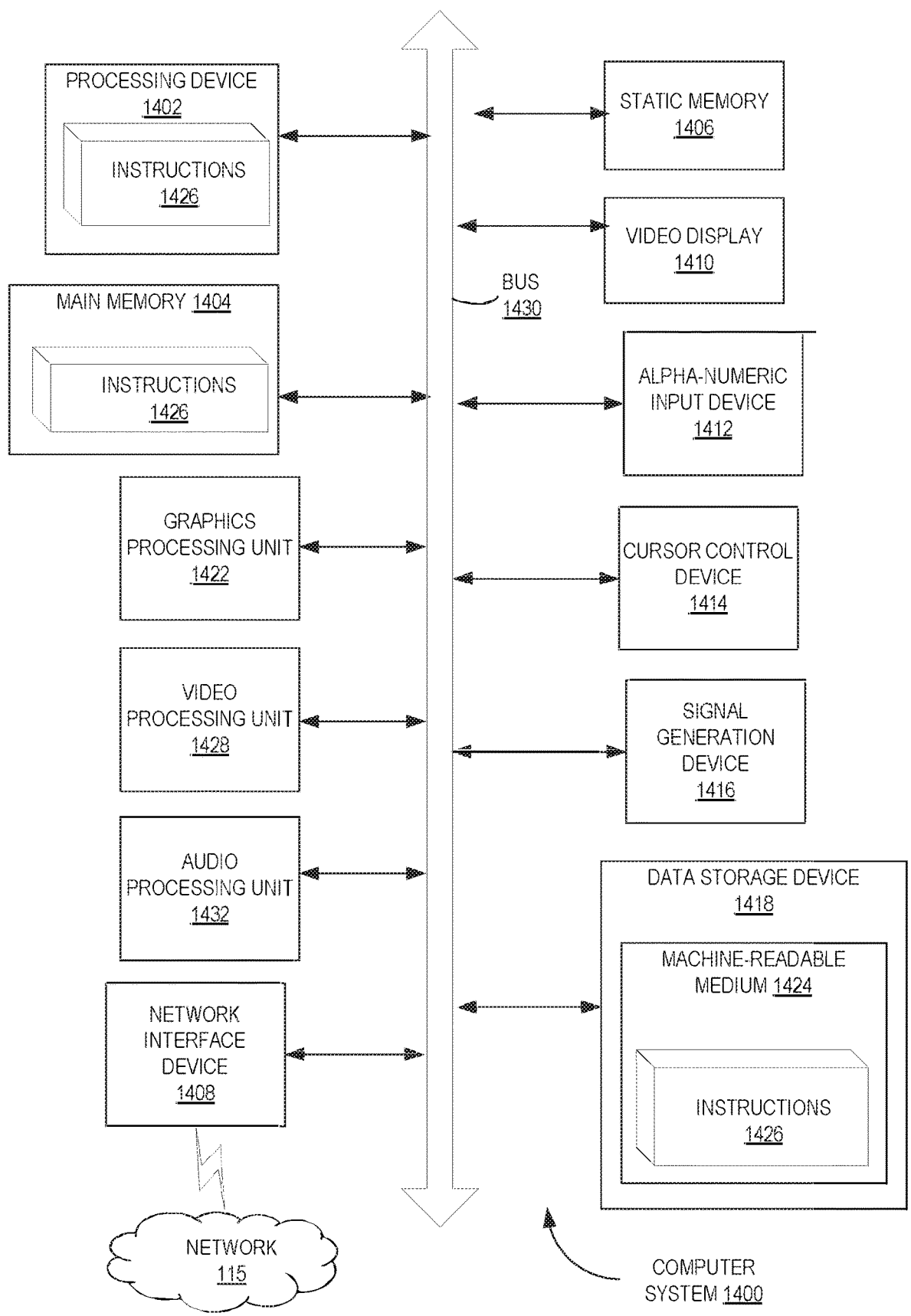
FIG. 14 illustrates a block diagram of one implementation of a computer system.

FIG. 14 illustrates a diagrammatic representation of a machine in the exemplary form of a computer system 1400 within which a set of instructions for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 1400 includes a processing device (processor) 1402, a main memory 1404 (e.g., read-only memory (ROM), flash memory, dynamic random access memory (DRAM) such as synchronous DRAM (SDRAM) or Rambus DRAM (RDRAM), etc.), a static memory 1406 (e.g., flash memory, static random access memory (SRAM), etc.), and a data storage device 1418, which communicate with each other via a bus 1430 or through another means such as a communication interface and/or direct connections.

Processing device 1402 represents one or more general-purpose processing devices such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a field programmable gate array (FPGA), a digital signal processor (DSP), network processor, or the like. The processing device 1402 is configured to execute instructions 1426 for performing the operations and steps discussed herein.

The computer system 1400 may further include a network interface device 1408. The computer system 1400 also may include a video display unit 1410 (e.g., a liquid crystal display (LCD), a cathode ray tube (CRT), or a touch screen), an alphanumeric input device 1412 (e.g., a keyboard), a cursor control device 1414 (e.g., a mouse), and a signal generation device 1416 (e.g., a speaker or other indictor(s)). The computer system 1400 may further include a graphics processing unit 1422, a video processing unit 1428 and an audio processing unit 1432.

The data storage device 1418 may include a machine-readable storage medium 1424 on which is stored one or more sets of instructions 1426 (e.g., software) embodying any one or more of the methodologies or functions described herein. The instructions 1426 may also reside, completely or at least partially, within the main memory 1404 and/or within the processing device 1402 during execution thereof by the computer system 1400, the main memory 1404 and the processing device 1402 also constituting computer-readable storage media. The instructions 1426 may further be transmitted or received over the communications network 115 via the network interface device 1408.

In one example, the communications network 115 may be a cellular network that may be a third generation partnership project (3GPP) release 8, 9, 10, 11, or 12 or Institute of Electronics and Electrical Engineers (IEEE) 802.16p, 802.16n, 802.16m-2011, 802.16h-2010, 802.16j-2009, 802.16-2009. In another embodiment, the communications network may be a wireless network (such as a wireless local area network (e.g., network using Wi-Fi® technology) that may follow a standard such as the IEEE 802.11-2012, IEEE 802.11ac, or IEEE 802.11ad standard. In another embodiment, the communications network may be a PAN connection (e.g., a connection using Bluetooth® technology) such as Bluetooth® v1.0, Bluetooth® v2.0, Bluetooth® v3.0, or Bluetooth® v4.0. In another embodiment, the communications network may be a PAN connection (e.g., a connection using the Zigbee® technology), such as IEEE 802.15.4-2003 (Zigbee® 2003), IEEE 802.15.4-2006 (Zigbee® 2006), IEEE 802.15.4-2007 (Zigbee® Pro). In one embodiment, the base station and the UMD may use near field communication, or induction communication to communicate information between the base station and the UMD.

While the machine-readable storage medium 1424 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer-readable storage medium, such as, but not limited to, any type of disk including floppy disks, optical disks, CD-ROMs, and magneto-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. A system, comprising:
a first sensor configured to generate first physiological data of a first user;
a second sensor configured to generate second physiological data of the first user;
a first processing device communicatively coupled to first sensor and the second sensor, wherein the first processing device is configured to:
receive the first physiological data from the first sensor and the second physiological data from the second sensor, wherein the first physiological data and the second physiological data are taken from the first user during a first time period;
determine a first correlation between the first physiological data and a first physiological parameter, wherein the first correlation comprises the first physiological data having a first value because the first physiological parameter is at a first level;
determine a second correlation between the second physiological data and the first physiological parameter, wherein the second correlation comprises the second physiological data having a second value because the first physiological parameter is at the first level;
make a first prediction of a change in the first physiological parameter according to the first correlation, the second correlation, or a combination of the first correlation and the second correlation, wherein:
the change is from the first level to a second level;
the prediction of the change in the level is for a second time period that:
immediately follows the first time period;
corresponds to the first time period on a subsequent day; or
occurs during a future day while the first user performs a similar or identical activity to an activity performed during the first time period; or
determine whether first environmental data is available;
in response to the environment data being available, receive the first environmental data including an environmental parameter, wherein the environmental parameter comprises:
an ambient temperature;
an ambient humidity;
an altitude;
a geographical location; or
a time of day;
determine a third correlation between the first environmental data and the first physiological parameter;
make a second prediction of the change in the level of the first physiological parameter according to a combination of:
the first correlation and the third correlation;
the second correlation and the third correlation; or
the first correlation, the second correlation, and the third correlation; and
to determine whether:
a first correlation level for the first correlation meets or exceeds a first threshold correlation level for the first correlation;
a second correlation level for the second correlation meets or exceeds a second threshold correlation level for the second correlation; or
a third correlation level for the third correlation meets or exceeds a third threshold correlation level for the third correlation, wherein:
in response to the first correlation level being below the first threshold correlation level, the processing device is configured to make the first prediction or the second prediction without the first correlation;
in response to the second correlation level being below the second threshold correlation level, the processing device is configured to make the first prediction or the second prediction without the second correlation; or
in response to the third correlation level being below the third threshold correlation level, the processing device is configured to make the second prediction without the third correlation.

2. The system of claim 1, wherein:
the first physiological data directly corresponds to a second physiological parameter that is different from the first physiological parameter; and
the second physiological data directly corresponds to a third physiological parameter that is different from the first physiological parameter and the second physiological parameter.

3. The system of claim 2, wherein:
the first physiological parameter is a hydration condition of the first user;
the first physiological data comprises an impedance spectroscopy measurement value; and
the second physiological data comprises an optical spectroscopy measurement value.

4. The system of claim 1, the first processing device further configured to generate a notification that indicates an action recommended for the first user based on the first prediction or the second prediction, wherein the action is a mitigation of the first prediction or the second prediction.

5. The system of claim 1, further comprising a second processing device communicatively coupled to the first processing device, wherein the second processing device is configured to:
receive a first baseline for the first physiological parameter, wherein the first baseline corresponds to the first user;
receive a second baseline for the first physiological parameter, wherein the second baseline corresponds to a second user;
receive the first prediction;
compare the first baseline to the second baseline; and
in response to the first baseline being within a threshold amount of the second baseline, make a third prediction for the second user, wherein the third prediction matches the first prediction.

6. The system of claim 5, the second processing device further configured to:
receive the second prediction;
determine whether second environmental data exists for the second user;
compare the second environmental data to the first environmental data; and
in response to the second environmental data existing for the second user and the second environmental data matching the first environmental data, make a fourth prediction for the second user, wherein the fourth prediction matches the second prediction.

7. A device, comprising:
a first sensor configured to generate first physiological data;
a second sensor configured to generate second physiological data;
a processing device coupled to the first sensor and the second sensor, wherein the processing device is configured to:
receive the first physiological data from the first sensor and the second physiological data from the second sensor, wherein the first physiological data and the second physiological data are taken from a user during a first time period;
determine a first correlation between the first physiological data and a physiological parameter;
determine a second correlation between the second physiological data and the physiological parameter;
make a first prediction of a change in a level of the physiological parameter according to the first correlation, the second correlation, or a combination of the first correlation and the second correlation, wherein the prediction of the change in the level is for a second time period after the first time period;
determine whether environmental data is available;
in response to the environment data being available, receive the environmental data including an environmental parameter;
determine a third correlation between the environmental data and the physiological parameter; and
make a second prediction of the change in the level of the physiological parameter according to a combination of:
the first correlation and the third correlation;
the second correlation and the third correlation; or
the first correlation, the second correlation, and the third correlation.

8. The device of claim 7, wherein the environmental parameter is:
a measurement of an ambient environmental condition in an immediate vicinity of the user; or
an activity of the user.

9. The device of claim 7, wherein the second time period:
is consecutive with the first time period;
is an analog of the first time period during a subsequent hour, day, week, or month; or
occurs while the user performs a similar activity to an activity performed during the first time period.

10. The device of claim 7, the processing device further configured to:
compare the first prediction or the second prediction to a baseline for the physiological parameter; and
in response to the first prediction or the second prediction being outside a threshold range of the baseline, generate a notification that the first prediction or the second prediction is outside the threshold range.

11. The device of claim 10, wherein the notification includes a recommended action for the user that will prevent the first prediction or the second prediction from occurring during the second time period.

12. The device of claim 7, wherein:
the first correlation comprises the first physiological data having a first value because the physiological parameter is at a level; or
the second correlation comprises the second physiological data having a second value because the physiological parameter is at the level.

13. The device of claim 7, wherein:
the first prediction is what a level of the physiological parameter will be when the environmental parameter is not present or is at a base level; or
the second prediction is what the level of the physiological parameter will be when the environmental parameter is present and has a known value.

14. A method, comprising:
receiving, at a processing device, first physiological data of a user and second physiological data of the user, wherein the first physiological data and the second physiological data are collected from the user;
determining, by the processing device, a first correlation between the first physiological data and a physiological parameter;
determining, by the processing device, a second correlation between the second physiological data and the physiological parameter;
receiving, at the processing device, first environmental data of an environment of the user;
determining, by the processing device, a third correlation between the first environmental data and the physiological parameter;
predicting, by the processing device, a change in a level of the physiological parameter according to the first correlation, the second correlation, or the third correlation; and
determining, by the processing device, a mitigating action for the user to perform to prevent or minimize the change in the level of the physiological parameter.

15. The method of claim 14, wherein:
the first physiological data or the second physiological data comprises historical data about the user recorded in a memory device and received at the processing device from the memory device; and the change in the level of the physiological parameter is predicted for a future time after the processing device predicts the change.

16. The method of claim 15, wherein the change in the level of the physiological parameter is predicted based on the future time corresponding to second environmental data that matches the first environmental data.

17. The method of claim 15, further comprising:
taking, by a sensor in communication with the processing device, a physiological measurement from the user;
determining, by the processing device, the physiological measurement matches the first physiological data or the second physiological data; and
generating a notification that notifies the user the change in the level of the physiological parameter is predicted to occur at the future time.

18. The method of claim 14, further comprising comparing the first correlation, the second correlation, or the third correlation to a threshold correlation, wherein the change is predicted in response to the first correlation, the second correlation, or the third correlation meeting or exceeding the threshold correlation.

\* \* \* \* \*